(12) United States Patent
Lee et al.

(10) Patent No.: US 8,653,279 B2
(45) Date of Patent: Feb. 18, 2014

(54) DYE FOR DYE-SENSITIZED SOLAR CELL, AND SOLAR CELL PREPARED FROM SAME

(75) Inventors: Jae-Kwan Lee, Yongin-si (KR); Ji-Won Lee, Yongin-si (KR); Jae-Jung Ko, Chungcheongnam-do (KR); Sang-Hoon Kim, Chungcheongnam-do (KR); Soo-Jin Moon, Yongin-si (KR); Moon-Sung Kang, Yongin-si (KR); Moon-Seok Kwon, Yongin-si (KR)

(73) Assignee: Samsung SDI Co., Ltd. (KR)

( * ) Notice: Subject to any disclaimer, the term of this patent is extended or adjusted under 35 U.S.C. 154(b) by 890 days.

(21) Appl. No.: 11/787,572

(22) Filed: Apr. 16, 2007

(65) Prior Publication Data

US 2007/0240756 A1   Oct. 18, 2007

(30) Foreign Application Priority Data

Apr. 17, 2006 (KR) .................. 10-2006-0034501
Mar. 12, 2007 (KR) .................. 10-2007-0024193

(51) Int. Cl.
*C07D 417/06* (2006.01)
*C07D 417/14* (2006.01)
*H01L 51/00* (2006.01)

(52) U.S. Cl.
USPC .............. 548/183; 549/59; 549/77; 8/550; 8/571; 8/575; 136/252; 136/263

(58) Field of Classification Search
USPC ................................ 8/550, 571, 575
See application file for complete search history.

(56) References Cited

U.S. PATENT DOCUMENTS

| | | | |
|---|---|---|---|
| 3,658,520 A | 4/1972 | Brantly et al. | |
| 6,130,310 A * | 10/2000 | Katayama et al. | 528/196 |
| 6,469,243 B2 * | 10/2002 | Yamanaka et al. | 136/263 |
| 7,659,410 B2 * | 2/2010 | Ohba et al. | 549/77 |
| 2003/0183271 A1 | 10/2003 | Ikeda et al. | |
| 2006/0130249 A1 * | 6/2006 | Ikeda et al. | 8/550 |

FOREIGN PATENT DOCUMENTS

| | | | |
|---|---|---|---|
| CA | 2579537 A1 * | 3/2006 | |
| DE | 1 908 345 | 2/1969 | |
| DE | 1 908 346 | 2/1969 | |
| EP | 0482884 | 4/1992 | |
| EP | 1628356 A1 | 2/2006 | |
| EP | 1990373 A1 | 11/2008 | |
| GB | 1 258 094 | 2/1968 | |
| JP | 2004/026757 A * | 1/2004 | |
| JP | 2004/099464 A * | 4/2004 | |
| JP | 2005-005026 A | 1/2005 | |
| JP | 2005-132914 A | 5/2005 | |
| KR | 2003-0026936 A | 4/2003 | |
| KR | 1020050119362 A | 12/2005 | |
| KR | 1020070016271 A | 2/2007 | |
| WO | WO-2004/082061 A1 * | 9/2004 | |
| WO | WO2007/100033 A1 | 9/2007 | |

OTHER PUBLICATIONS

An English translation of JP 2004/099464, 2004.*
An English translation of JP 2004/026757, 2004.*
Chinese Office Action for Chinese Application No. 200710096444X; dated Aug. 21, 2009; 7 pgs.
Kim et al., "Molecular Engineering of Organic Sensitizers for Solar Cell Applications", JACS Articles, J.AM.Chem.Soc, vol. 128, Dec. 5, 2006, pp. 16701-16707, Dec. 27, 2006.
Choi et al., "Novel organic dyes containing bis-dimethylfluorenyl amino benzo[b]thiophene for highly efficient dye-sensitized solar cell", ScienceDirect; Thetrahedron 63 (2007) pp. 3115-3121, Apr. 9, 2007.
Jung et al., "Synthesis and Photovoltaic Properties of Efficient Organic Dyes Containing the Benzo[b]furan Moiety for Solar Cells", JOCArticle, J. Org. Chem. 2007, 72, 3652-3658.
German Office Action for Application No. 102007019022.2; Applicant: Samsung Display Co., Ltd., dated Jun. 9, 2010, 4 pgs.
SIPO Second Office Action dated Dec. 14, 2010 for Application No. 200710096444.X.
Japanese Office Action corresponding to Application No. 2007-108553 dated Dec. 7, 2010, 4 pages, No translation provided.
Decision of Rejection issued by The State Intellectual Property Office of P.R. China dated Jun. 13, 2012, 9 pages.
German Office Action issued by the German Patent and Trademark Office dated Jan. 30, 2013, 3 pages.
SIPO Office Action dated Nov. 2, 2011.
KIPO Notice of Allowance issued by the Korean Patent Office dated Dec. 14, 2012, 5 pages.
Office Action issued by the State Intellectual Property Office of P.R. China on Sep. 5, 2013 in the corresponding Chinese Application No. 200710096444.X in 18 pages.

* cited by examiner

*Primary Examiner* — Laura L. Stockton
(74) *Attorney, Agent, or Firm* — Knobbe Martens Olson & Bear, LLP

(57) ABSTRACT

The present embodiments relate to a dye for a dye-sensitized solar cell and a dye-sensitized solar cell prepared from the same. The dye includes a fluorenyl-containing compound. The dye according to the present embodiments is applied to a light absorption layer to improve photovoltaic efficiency and increase an open-circuit voltage.

3 Claims, 3 Drawing Sheets

DYE FOR DYE-SENSITIZED SOLAR CELL, AND SOLAR CELL PREPARED FROM SAME

CROSS-REFERENCES TO RELATED APPLICATIONS

This application claims priorities to and the benefits of Korean Patent Application No. 10-2006-0034501 filed in the Korean Intellectual Property Office on Apr. 17, 2006 and Korean Patent Application No. 10-2007-0024193 filed in the Korean Intellectual Property Office on Mar. 12, 2007, the entire contents of which are incorporated herein by reference.

BACKGROUND OF THE INVENTION

1. Field of the Invention

The present embodiments relate to a dye (photosensitizer) for a dye-sensitized solar cell and a dye-sensitized solar cell prepared from the same. More particularly, the present embodiments relate to a dye for a dye-sensitized solar cell that is capable of improving photovoltaic efficiency, an open-circuit voltage of a solar cell, and a dye-sensitized solar cell with improved photoelectric efficiency.

2. Description of the Related Art

Diverse research has been carried out in an attempt to develop energy sources that can replace conventional fossil fuels and solve the approaching energy crisis. Particularly, extensive research is underway to find alternative energy sources, such as wind power, atomic power, and solar power, as substitutes for petroleum resources, which are expected to be depleted within several decades. Among the alternative energy sources, solar cells use solar energy that is essentially infinite and environmentally friendly, as opposed to other energy sources. Since 1983 when a Se solar cell was first produced, solar cells have been highlighted, and Si solar cells have recently been drawing attention from researchers.

However, it is difficult to practically use Si solar cells because the production cost is high and there are difficulties in improving cell efficiency. To overcome the problem, researchers are studying development of a dye sensitized solar cell that can be produced at a low cost.

Different from the Si solar cell, the dye sensitized solar cell is an electrochemical solar cell that is mainly composed of photosensitive dye molecules that absorb visible rays and produce electron-hole pairs, and a transition metal oxide that transfers the produced electrons. Among conventional dye sensitized solar cells is a dye sensitized solar cell using nano titanium oxide, i.e., anatase, which was developed by Michael Gratzel et al. of the Swiss Federal Institute of Technology, Lausanne (EPFL), Switzerland, in 1991.

The dye sensitized solar cell can be produced at a low cost, and since it uses a transparent electrode, there is an advantage in that it can be applied to external glass walls of a building or a glass greenhouse. However, the dye sensitized solar cell has a limitation in application for practical use due to low photoelectric efficiency.

The photoelectric efficiency of a solar cell is in proportion to the quantity of electrons produced from the absorption of solar beams. Thus, to increase the photoelectric efficiency, the quantity of electrons should be increased or the produced and excited electrons should be prevented from being used to cause electron-hole recombination. The quantity of produced electrons can be increased by raising the absorption of solar beams or the dye adsorption efficiency.

Particles of an oxide semiconductor should be prepared in a nano-size to increase the dye adsorption efficiency of each unit area, and the reflectivity of a platinum electrode should be increased or a micro-sized oxide semiconductor light scattering agent should be included to increase the absorption of solar beams. However, since the conventional methods have a limitation in increasing the photoelectric efficiency of solar cells, it is required to develop new technology that can improve the photoelectric efficiency.

SUMMARY OF THE INVENTION

One embodiment provides a dye for a dye-sensitized solar cell having a high open-circuit voltage.

Another embodiment provides a dye sensitized solar cell including the dye and thereby having improved photoelectric efficiency.

According to one embodiment, a dye for a dye-sensitized solar cell having the following Formula 1:

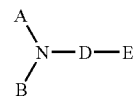

[Chemical Formula 1]

wherein, in the above Formula 1,

A and B are independently selected from the group consisting of a substituted or unsubstituted aromatic hydrocarbons, a substituted or unsubstituted heterocycles, D is selected from the group consisting of a substituted or unsubstituted cycloalkylene, a substituted or unsubstituted alkenylene, a substituted or unsubstituted arylene, a substituted or unsubstituted divalent heterocycle, and E is an acidic functional group.

In another embodiment, A and B are independently selected from the group consisting of a substituted or unsubstituted $C_5$ to $C_{20}$ aromatic hydrocarbon, a substituted or unsubstituted $C_5$ to $C_{20}$ heterocycle. According to one embodiment, at least one of the A and B is fluorenyl.

In another embodiment, A and B may independently include at least one substituent selected from the group consisting of a hydroxyl, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and heterocycle.

In another embodiment, D is selected from the group consisting of a substituted or unsubstituted $C_3$ to $C_{18}$ cycloalkylene; a substituted or unsubstituted $C_2$ to $C_{20}$ alkenylene; a substituted or unsubstituted $C_6$ to $C_{30}$ arylene; a substituted or unsubstituted divalent heterocycle including a heteroatom selected from the group consisting of oxygen, sulfur, and nitrogen.

In another embodiment, D may independently include at least one substituent selected from the group consisting of a hydroxyl, a halogen, a nitro, a cyano, an amino, an acyl, an acyloxy, a carboxyl, a sulfonyl, an alkyl, a cycloalkyl, a haloalkyl, an alkysulfonyl, an alkylthio, an alkoxy, an alkoxysulfonyl, an alkoxycarbonyl, an aryl, an aryloxy, an alkenyl, an aralkyl, and heterocycle.

According to one embodiment, D is selected from the group consisting of the following Formulae 2 to 4.

[Chemical Formula 2]

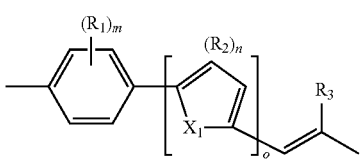

[Chemical Formula 3]

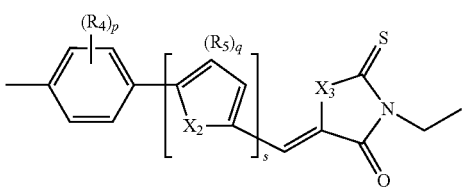

[Chemical Formula 4]

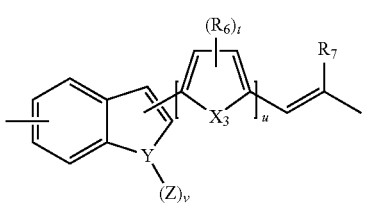

Wherein, $R_1$ to $R_7$ are independently selected from the group consisting of a hydrogen, a hydroxyl, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, alkenyl, an aralkyl, a heterocycle, $X_1$ to $X_3$ are independently selected from the group consisting of oxygen or sulfur, Y is selected from the group consisting of oxygen, sulfur, and nitrogen, Z is selected from the group consisting of a substituted or unsubstituted aromatic hydrocarbon, a substituted or unsubstituted heterocycle, m and p are independently an integer ranging from 1 to 4, n, q, and t are independently 1 or 2, o, s, and u are independently an integer ranging from 0 to 4, and v is 0 or 1.

In the above Formula 4, Z may independently include at least one substituent selected from the group consisting of a hydroxyl, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and heterocycle.

According to one embodiment, E may include be substituent selected from the group consisting of carboxyl, phosphorous acid, sulfonic acid, phosphinic acid, hydroxyl, oxycarboxylic acid, acid amide, boric acid, and squaric acid. According to another embodiment, E is carboxyl.

According to one embodiment, a dye where at least one of the A and B is fluorenyl; and D is represented by one selected from the group consisting of the above Formulae 2 to 4; and E is carboxyl is provided.

According to another embodiment, a dye selected from the group consisting of the following Formulae 5 to 10 and mixtures thereof is provided.

[Chemical Formula 5]

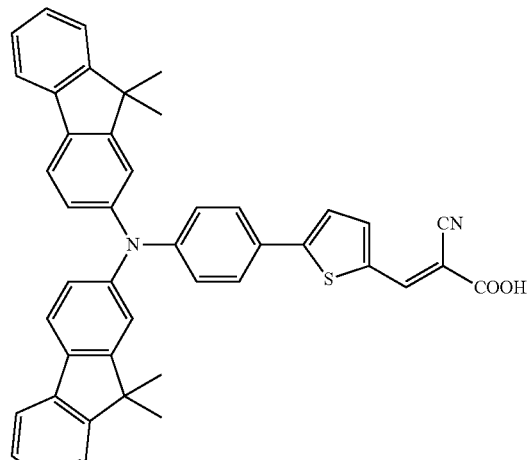

[Chemical Formula 6]

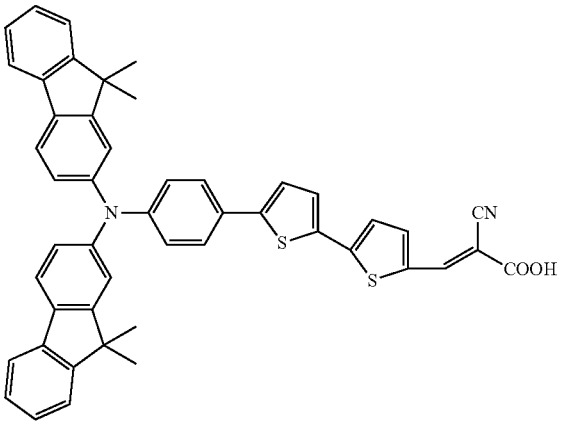

[Chemical Formula 7]

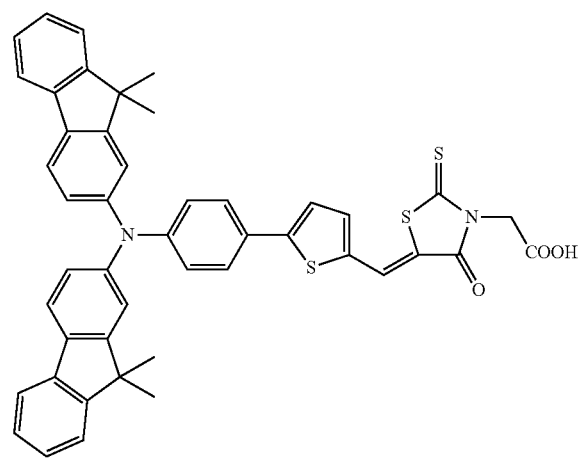

[Chemical Formula 8]

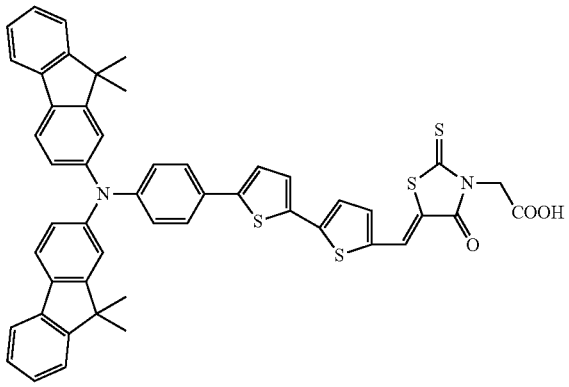

[Chemical Formula 9]

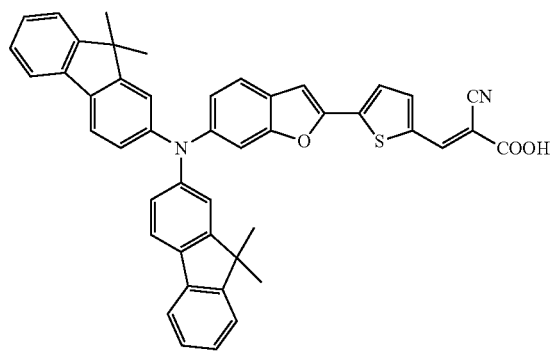

[Chemical Formmual 10]

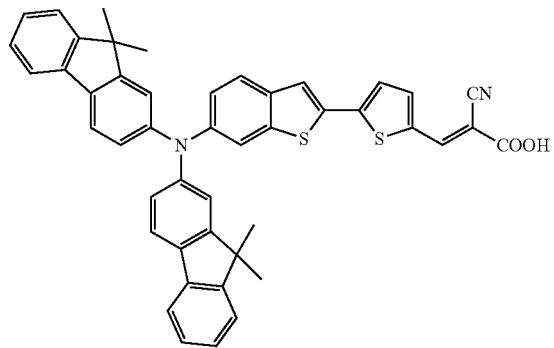

According to another embodiment, provided is a dye-sensitized solar cell that includes a first electrode including a conductive transparent substrate; a light absorption layer formed on one side of the first electrode; a second electrode opposite to the first electrode with the light absorption layer; and an electrolyte positioned in a space between the first and second electrodes. The light absorption layer includes a semiconductor particulate and the above dye.

In another embodiment, the first electrode includes a transparent substrate; and a conductive layer disposed on the transparent substrate. The conductive layer may include a conductive metal oxide selected from the group consisting of indium tin oxide (TO), fluorine tin oxide (FTO), ZnO—($Ga_2O_3$ or $Al_2O_3$), a tin-based oxide, antimony tin oxide (ATO), zinc oxide, and combinations thereof.

The transparent substrate may be a glass or plastic substrate.

Examples of the plastic substrate may be selected from the group consisting of polyethylene terephthalate, polyethylene naphthalate, polycarbonate, polypropylene, polyimide, triacetylcellulose, polyethersulfone, and mixtures thereof.

The semiconductor particulate may be an elementary substance semiconductor, a compound semiconductor, a perovskite compound, or mixtures thereof.

Examples of the compound semiconductor include an oxide including at least one metal selected from the group consisting of Ti, Zr, Sr, Zn, In, Yr, La, V, Mo, W, Sn, Nb, Mg, Al, Y, Sc, Sm, Ga, In, TiSr, and combinations thereof.

The semiconductor particulate may be selected from the group consisting of Si, $TiO_2$, $SnO_2$, ZnO, $WO_3$, $Nb_2O_5$, $TiSrO_3$, and combinations thereof.

The semiconductor particulate has an average particle diameter of 50 nm or less.

The light absorption layer may further include an additive selected from the group consisting of the compounds represented by the following Formula 11.

$$Q\text{-}CO_2H \quad \text{[Chemical Formula 11]}$$

Wherein in the above Formula 11, Q is selected from the group consisting of an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, aralkyl, and heterocycle.

According to one embodiment, the additive may be deoxycholic acid.

The additive may be used in an amount of about 100 to about 3000 parts by weight based on 100 parts by weight of the dye.

The light absorption layer 12 may have a thickness of about 25 μm or less.

The second electrode may include a material selected from the group consisting of Pt, Au, Ni, Cu, Ag, In, Ru, Pd, Rh, Ir, Os, C, a conductivity polymer, and combinations thereof.

As used herein, the term "alkyl" refers to a $C_1$ to $C_{20}$ alkyl, the 'cycloalkyl' refers to a $C_3$ to $C_{20}$ cycloalkyl, the 'alkoxy' refers to a $C_1$ to $C_{20}$ alkoxy, the 'aryl' refers to a $C_6$ to $C_{30}$ aryl, the 'alkenyl' refers to a $C_2$ to $C_{20}$ alkenyl, 'aralkyl' refers to a $C_6$ to $C_{30}$ aralkyl, the 'alkylene' refers to a $C_1$ to $C_{20}$ alkylene, 'cycloalkylene' refers to substituted or unsubstituted a $C_3$ to $C_{18}$ cycloalkylene, the 'alkenylene' refers to a $C_2$ to $C_{20}$ alkenylene, and the 'alkylene' refers to a $C_6$ to $C_{30}$ arylene.

As used herein, the term "substituted" refers to a compound substituted with a substituent selected from the group consisting of a hydroxyl, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, alkenyl, arakyl, and heterocycle.

DETAILED DESCRIPTION OF THE EMBODIMENTS

Figure 1:
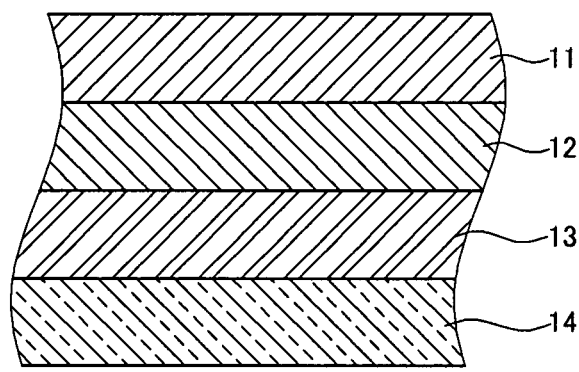
FIG. 1 is a schematic view showing a dye sensitized solar cell according to one embodiment.

Exemplary embodiments will hereinafter be described in detail with reference to the accompanying drawings.

During driving of a dye-sensitized solar cell, photocharges are generated by optical energy. In general, the photocharges are generated by dye materials. The dye materials are excited by absorbing light that transmits through a conductive transparent substrate.

For the dye materials, metal composites such as a mono (substituted 2,2'-bipyridine), bis(substituted 2,2'-bipyridine) or tris(substituted 2,2'-bipyridine) complex salt of ruthenium are generally used. However, these metal composites have a problem of low efficiency since electrons excited by light are quickly restored to a ground state. In order to solve these problems, there has been much research into metal composites linked with various electron transferring materials through covalent bonds. However, linking the electron transferring material through covalent bonds is implemented by complex processes.

According to one embodiment, a dye that includes aniline having a fluorenyl functional group instead of an alkyl group, or a compound including a benzofuran group, a benzothiophene group, or an indole functional group instead of a phenyl group is provided which improves photoelectric efficiency of a dye-sensitized solar cell.

The dye for a dye-sensitized solar cell according to one embodiment is represented by the following Formula 1:

[Chemical Formula 1]

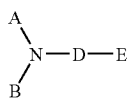

wherein, in the above Formula 1,

A and B are independently selected from the group consisting of substituted or unsubstituted aromatic hydrocarbons, substituted or unsubstituted heterocycles, D is selected from the group consisting of a substituted or unsubstituted cycloalkylene, a substituted or unsubstituted alkenylene, a substituted or unsubstituted arylene, a substituted or unsubstituted divalent heterocyclic group, and E is an acidic functional group.

In the above Formula 1, A and B are preferentially independently selected from the group consisting of a substituted or unsubstituted $C_5$ to $C_{20}$ aromatic hydrocarbon, a substituted or unsubstituted $C_5$ to $C_{20}$ heterocycle.

The aromatic hydrocarbon may be selected from the group consisting of phenyl, naphthyl, xylyl, anthryl, phenanthryl, naphthacenyl, pyrenyl, biphenylyl, terphenylyl, tolyl, fluorenyl, indenyl, perylenyl, and combinations thereof.

The heterocycle may include an element selected from the group consisting of oxygen, sulfur, nitrogen and combinations thereof. According to one embodiment, the heterocycle may be selected from the group consisting of thiazolyl, benzothiazolyl, naphtothiazolyl, benzoxazolyl, naphtoxazolyl, imidazolyl, benzimidazolyl, naphtoimidazolyl, thiazolyl, pyrrolyl, pyrazinyl, pyridyl, indolyl, isoindolyl, furyl, benzofuryl, isobenzofuryl, quinolyl, isoquinolyl, quinoxalinyl, carbazolyl, phenanthridinyl, acridinyl, phenanthrolinyl, phenazinyl, phenothiazinyl, phenoxazinyl, oxazolyl, oxadiazolyl, furazanyl, thienyl, and combinations thereof.

In a preferred embodiment, at least one of A and B is fluorenyl.

A and B may independently include at least one substituent selected from the group consisting of a hydroxyl, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and a heterocycle.

In some embodiments the amino substituent can be a functional group represented by $—NX_1X_2$, where $X_1$ and $X_2$ may be a substituent selected from the group consisting of hydrogen, a halogen, an alkyl, and an acyl. According to one embodiment, the amino substituent may be selected from the group consisting of N-methylamino, N-ethylamino, N,N-diethylamino, N,N-diisopropylamino, N,N-dibutylamino, N-benzylamino, N,N-dibenzylamino, N-phenylamino, N-phenyl-N-methylamino, N,N-diphenylamino, N,N-bis(m-tolyl)amino, N,N-bis(p-tolyl)amino, N,N-bis(p-phenylyl)amino, bis[4-(4-methyl)biphenyl]amino, N—N-biphenyl-N-phenylamino, N-α-naphthyl-N-phenylamino, N-β-naphthyl-N-phenylamino, N-phenanthryl-N-phenylamino, and acetylamino.

The acyl group is a functional group represented by —OCR. According to one embodiment, the acyl group may be selected from the group consisting of acetyl, phenoxycarbonyl, and methoxycarbonyl.

The acyloxy group is a functional group represented by —OCOR. According to one embodiment, the acyloxy group may be selected from the group consisting of acetyloxy, benzoyloxy, octadecanoyloxy, cyclohexylcarbonyloxy, and phenylcarbamoyloxy.

The alkyl group may be selected from the group consisting of $C_1$ to $C_{20}$ substituted or unsubstituted alkyl. According to one embodiment, the alkyl is selected from the group consisting of $C_1$ to $C_{12}$ substituted or unsubstituted alkyl. The alkyl may be a $C_1$ to $C_6$ lower alkyl such as methyl, ethyl, n-propyl, isopropyl, n-butyl, isobutyl, sec-butyl, t-butyl, pentyl, isoamyl, or hexyl. According to one embodiment, the alkyl may be a $C_1$ to $C_3$ lower alkyl.

The cycloalkyl group may be a $C_3$ to $C_{20}$ cyclic alkyl, such as cyclopropyl, cyclobutyl, and cyclopentyl.

The haloalkyl group is an alkyl substituted with a halogen atom, where the halogen refers to F, Cl, Br, or I, and the alkyl is the same as in the definition as above.

The alkylsulfonyl group is represented by $R—SO_2—$, and the definition of the alkyl (R) is the same as above. The alkylsulfonyl group may include a $C_1$ to $C_{12}$ substituted or unsubstituted alkyl. According to one embodiment, the alkylsulfonyl group may be selected from the group consisting of methylsulfonyl, octylsulfonyl, ethylhexyl sulfonyl.

The alkylthio group is represented by $R—S—$, and the definition of the alkyl (R) is the same as above. The alkylthio group may include a $C_1$ to $C_{12}$ substituted or unsubstituted alkyl.

The alkoxy group may be selected from the group consisting of an oxygen-containing substituted or unsubstituted alkoxy that includes a $C_1$ to $C_{20}$ alkyl. According to one embodiment, the alkoxy group may be selected from the group consisting of a $C_1$ to $C_6$ lower alkoxys such as methoxy, ethoxy, propoxy, butoxy, t-butoxy, and the like. The alkoxy group may be a haloalkoxy that has a substituent of at least one halogen such as fluoro, chloro, or bromo. The alkoxy group may be a $C_1$ to $C_3$ haloalkoxy such as fluoromethoxy, chloromethoxy, trifluoromethoxy, trifluoroethoxy, fluoroethoxy, or fluoropropoxy.

The alkoxysulfonyl group is a sulfonyl including alkoxy, and the definition of the alkoxy group is the same as above. According to one embodiment, the alkoxysulfonyl group may be selected from the group consisting methoxysulfonyl, and phenoxysulfonyl.

The alkoxycarbonyl group is represented by $—COOX_3$, where the $X_3$ may be a substituent selected from the group consisting of hydrogen, a halogen, an alkyl, and an acyl.

The aryl group may be a $C_6$ to $C_{30}$ carbocycle aromatic based compound including at least one cycle such as phenyl, naphthyl, tetrahydronaphthyl, indanyl, and biphenyl. The aryl can be used individually or in combination and the cycle may be bound as a pendent group or fused. According to one embodiment, the aryl may be phenyl. The aryl may have 1 to 3 substituents such as hydroxy, halo, haloalkyl, nitro, cyano, alkoxy, and a $C_1$ to $C_6$ lower alkylamino.

The aryloxy group is represented by aryl-O—, and the definition of the alkyl is the same as above.

The alkenyl group refers to a $C_2$ to $C_{20}$ alkenyl. According to one embodiment, the alkenyl may be selected from the group consisting of a vinyl, an allyl, a 1-butenyl, a 1,3-butadienyl, a 1-methylvinyl, and a styryl.

The aralkyl group may be selected from the group consisting of benzyl, 1-phenylethyl, 2-phenylethyl, phenylisopropyl, methylbenzyl, 1-α-naphthylethyl, aminobenzyl, hydroxybenzyl, chlorobenzyl, cyanobenzyl, naphthylisopropyl.

The heterocycle group is the same as defined above.

In the Formula 1, D may be a substituted or unsubstituted divalent heterocyclic group and combination thereof that includes an element selected from the group consisting of a substituted or unsubstituted $C_3$ to $C_{18}$ cycloalkylene, a substituted or unsubstituted $C_2$ to $C_{20}$ alkenyl, a substituted or unsubstituted $C_6$ to $C_{30}$ arylene, an oxygen, a sulfur, and a nitrogen.

According to one embodiment, D may include be at least one selected from the group consisting of a vinyl group, a polyvinyl group, benzene, naphthalene, anthracene, pyrene, phenanthrene, indene, perylene, fluorene, biphenyl, terphenyl, pyridine, pyrazine, pyrimidine, pyrazole, pyrazolidine, pyran, pyrrole, benzoimidazole, imidazoline, imidazolidine, imidazole, triazol, triazine, diazol, morpholine, thiophene, thiazole, benzothiazole, naphthothiazole, benzoxazole, naphthooxazole, pyrazine, quinoline, quinazoline, and carbazole.

D may include a substituent selected from the group consisting of a hydroxy, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and heterocycle. In some embodiments, the substituent of D is the same as in the definition of A and B.

The D group may be a compound selected from the group consisting of the following Formulae 2 to 4.

[Chemical Formula 2]

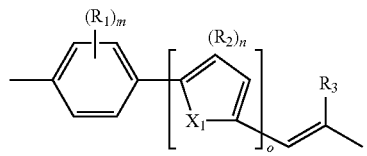

[Chemical Formula 3]

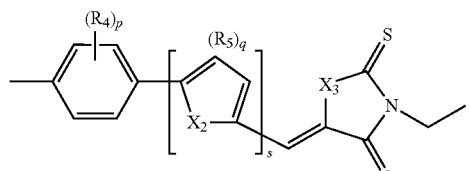

[Chemical Formula 4]

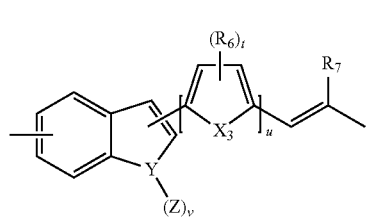

Wherein, $R_1$ to $R_7$ are independently selected from the group consisting of hydrogen, a hydroxy, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and a heterocycle.

$X_1$ to $X_3$ are independently oxygen or sulfur,

Y is selected from the group consisting of oxygen, sulfur and nitrogen,

Z is selected from the group consisting of a substituted or unsubstituted aromatic hyrocarbon, a substituted or unsubstituted heterocycle.

m and p are an integer independently ranging from 1 to 4, n, q, and t are independently 1 or 2, o, s, and u are an integer independently ranging from 0 to 4, and v is 0 or 1.

Wherein, in the above formula, the Z may include be substituted with at least one substituent selected from the group consisting of a hydroxyl, a halogen, a nitro, a cyano, an amino, an acyl, an acyloxy, a carboxyl, a sulfonyl, an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and a heterocycle.

According to one embodiment, t and u are 1 or 2.

E is an acidic functional group. According to one embodiment, E may be selected from the group consisting of carboxyl, phosphorous acid, sulfonic acid, phosphinic acid, hydroxy, oxycarboxylic acid, acid amide, boric acid, and squaric acid. According to one embodiment, E is carboxyl.

According to another embodiment, in the above Formula 1, at least one of A and B are a substituted or unsubstituted fluorenyl, D has a structure selected from the group consisting of above Formulae 2 to 4, and E is a carboxyl. According to yet another embodiment, both A and B are a substituted or unsubstituted fluorenyl.

According to yet embodiment, the dye may be selected from the group consisting of a compounds represented by the following Formulae 5 to 10 and mixtures thereof:

[Chemical Formula 5]

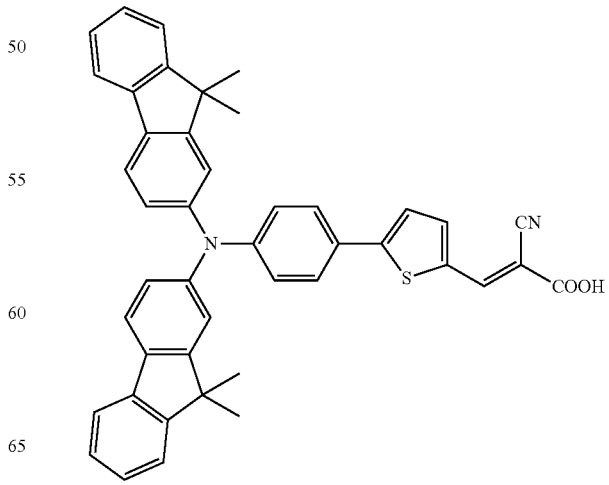

[Chemical Formula 6]

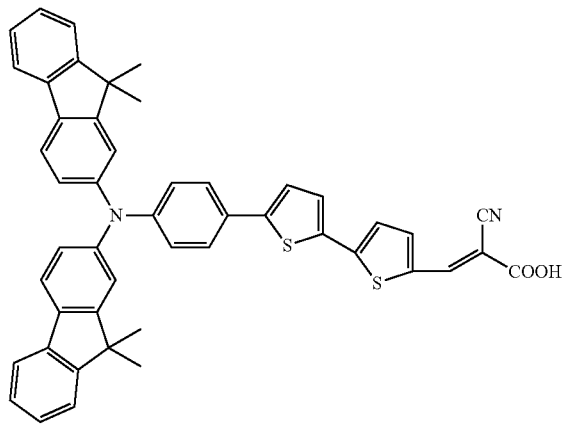

[Chemical Formula 7]

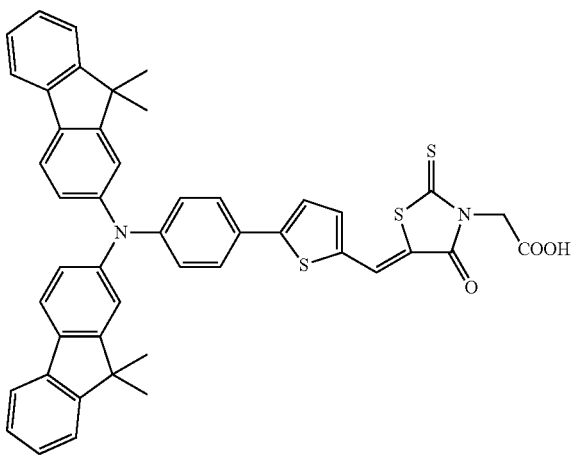

[Chemical Formula 8]

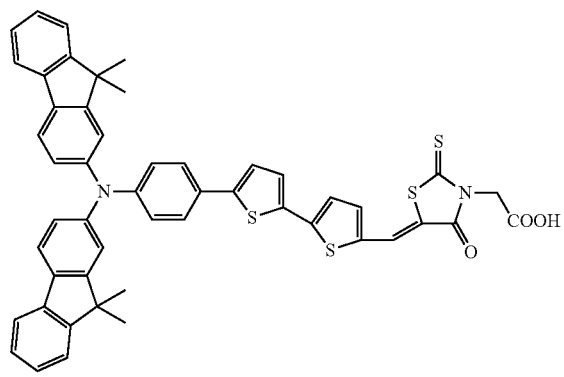

[Chemical Formula 9]

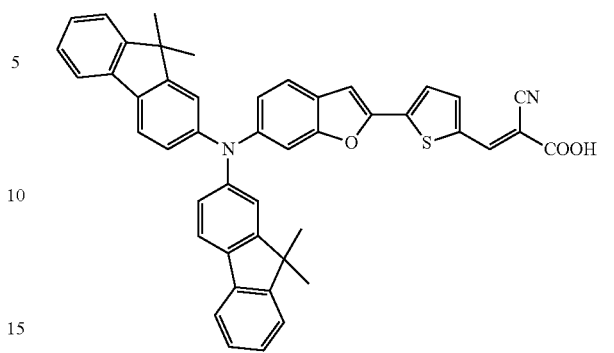

[Chemical Formula 10]

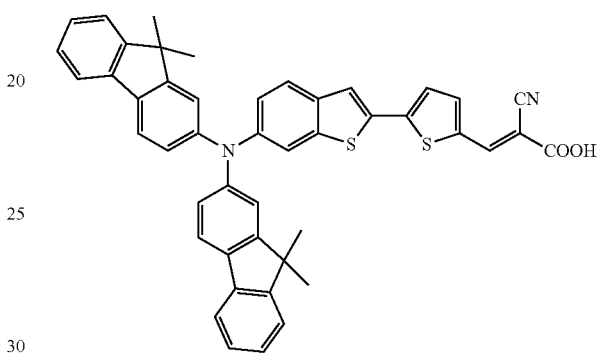

In one embodiment, the dye that includes aniline having a fluorenyl functional group instead of an alkyl group or a compound having benzofuran, benzothiophene or a indole functional group instead of a phenyl are applied to a light absorbing layer of dye-sensitized solar cell and thereby can improve photoelectric efficiency and open-circuit voltage of a dye-sensitized solar cell.

The present embodiments also provide a dye-sensitized solar cell including the dye.

The dye-sensitized solar cell includes a first electrode including a conductive transparent substrate; a light absorption layer formed on one side of the first electrode; a second electrode opposite to the first electrode with the light absorption layer therebetween; and an electrolyte positioned in a space between the first electrode and the second electrode. The light absorption layer includes a semiconductor particulate and any herein described dye.

FIG. 1 is a cross-sectional view showing a structure of a dye sensitized solar cell in accordance with an exemplary embodiment.

The dye sensitized solar cell 10 has a sandwich structure where two plate-type transparent electrodes, which are a first electrode 11 and a second electrode 14 respectively, contact each other surface to surface. One side of one transparent electrode of the two transparent electrodes 11 and 14, e.g., the first electrode 11, includes a light absorption layer 12, which includes a semiconductor particulate and a photosensitive dye that is adsorbed to the semiconductor particulate. The electrons of the photosensitive dye are excited by absorbing visible rays. The space between the two electrodes 11 and 14 is filled with an electrolyte 13 for an oxidation-reduction reaction.

When solar beams enter the dye sensitized solar cell, dye molecules in the light absorption layer 12 absorb photons. The dye molecules that have absorbed the photons are excited from a ground state, which is called electron transfer, to thereby form electron-hole pairs. The excited electrons are injected into a conduction band on the semiconductor particulate interface. The injected electrons are transferred to the first electrode 11 through the interface and then they are transferred to the second electrode 14, which is an electrode opposite to the first electrode 11, through an external circuit. The dye that is oxidized as a result of the electron transfer is reduced by ions of an oxidation-reduction couple in the electrolyte 13, and the oxidized ions are involved in a reduction reaction with electrons that have arrived at the interface of the second electrode 14 to achieve charge neutrality. The dye sensitized solar cell is operated as described above.

The first electrode (working electrode, semiconductor electrode) 11 includes a transparent substrate and a conductive layer disposed on the transparent substrate.

The transparent substrate may be formed of any transparent material to transmit external light, such as glass or plastic. Non-limiting examples of the plastics may be selected from the group consisting of polyethylene terephthalate (PET), polyethylene naphthalate (PEN), polycarbonate (PC), polypropylene (PP), poly imide (PI), triacetyl cellulose (TAC), copolymers thereof, and combinations thereof.

The transparent substrate may be doped with a doping material selected from the group consisting of Ti, In, Ga, and Al.

A conductive layer is positioned on the transparent substrate.

The conductive layer may include a conductive metal oxide selected from the group consisting of indium tin oxide (ITO), fluorine tin oxide (FTO), ZnO—($Ga_2O_3$ or $Al_2O_3$), tin oxide, antimony tin oxide (ATO), zinc oxide, $SnO_2$ and combinations thereof. However, the present embodiments are not so limited and any material would be appropriate if it has excellent conductivity, transparency, and heat resistance.

The conductive layer may include a single layered or a multi-layered conductive metal oxide.

In the embodiment, the light absorption layer 12 includes semiconductor particulate and the dye. The dye of the present embodiments is adsorbed to the semiconductor particulate, and the electrons of the dye are excited by the absorption of visible rays.

The semiconductor particulate may be of an elementary substance semiconductor, which is represented by silicon, compound semiconductor, or a perovskite (CaTiO3) metal oxide composite.

The semiconductor may be an n-type semiconductor in which electrons of the conduction band become a carrier by being optically excited and provide an anode current. Examples of the compound semiconductor include an oxide including at least one metal selected from the group consisting of Ti, Zr, Sr, Zn, In, Yr, La, V, Mo, W, Sn, Nb, Mg, Al, Y, Sc, Sm, Ga, In, TiSr, and combinations thereof. Examples of the semiconductor particulate include Si, $TiO_2$, $SnO_2$, ZnO, $WO_3$, $Nb_2O_5$, and $TiSrO_3$, and in a preferred embodiment the semiconductor particulate may be anatase $TiO_2$. The semiconductor is not limited to the above-mentioned materials, and the above-mentioned materials may be used individually or in combination.

The semiconductor particulate may have a large surface area to make the dye adsorbed onto the surface of the semiconductor particulate absorb much light. Specifically, the semiconductor particulate may have an average particle diameter of less than or equal to about 50 nm. According to one embodiment, the semiconductor particulate may have an average particle diameter of from about 15 nm to about 25 nm.

The dye can be any as described above.

The light absorption layer may further include at least one additive selected from the group consisting of compounds having the following formula 11 in order to improve photoelectric efficiency of a solar cell.

[Chemical Formula 11]

In the above Formula 11, Q is selected from the group consisting of an alkyl, a cycloalkyl, a haloalkyl, an alkylsulfonyl, an alkylthio, an alkoxy, an alkoxysulfonyl, an alkoxycarbonyl, an aryl, an aryloxy, an alkenyl, an aralkyl, and heterocycle.

According to one embodiment, the additive may be deoxycholic acid having the following Formula 12.

[Chemical Formula 12]

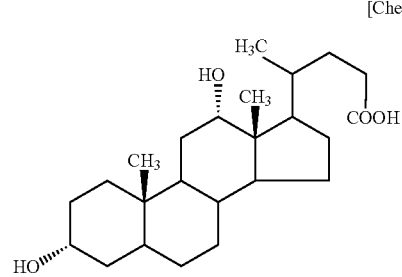

The additive may be used in an amount of from about 100 to about 3000 parts by weight based on 100 parts by weight of the dye. According to one embodiment, the additive may be used in an amount of from about 100 to about 2000 parts by weight based on 100 parts by weight of the dye.

Further, the light absorption layer 12 may have a thickness of about 25 µm or less. According to another embodiment, the thickness ranges from about 1 to about 25 µm. According to yet another embodiment, the thickness ranges from about 5 to about 25 µm.

The second electrode 14, which may be a counter electrode, can be formed of any material that has a conductive property. Even if the material is an insulating material, if a conductive layer is formed on a side facing the first electrode, it can be used as the second electrode. In some embodiments, the second electrode 14 can be formed of at least one material selected from the group consisting of Pt, Au, Ni, Cu, Ag, In, Ru, Pd, Rh, Ir, Os, C, conductive polymers, and combinations thereof.

The second electrode 14 includes a transparent substrate and a transparent electrode facing the first electrode 11, and a catalyst electrode (not shown) formed on the transparent electrode.

The transparent substrate may be composed of a glass or a plastic as in the first electrode. Specific examples of the plastic may include polyethylene terephthalate, polyethylene naphthalate, polycarbonate, polypropylene, polyimide, triacetylcellulose, polyethersulfone, and the like.

On the transparent substrate, a transparent electrode is disposed. The transparent electrode may be formed of a transparent material such as indium tin oxide, fluorine tin oxide, antimony tin oxide, zinc oxide, tin oxide, ZnO—$Ga_2O_3$, ZnO—$Al_2O_3$, and the like. The transparent electrode may be composed of a mono-layered membrane or a multi-layered membrane.

In some embodiments, a catalyst electrode is disposed on the transparent electrode. The catalyst electrode activates a redox couple, and includes a conductive material selected from the group consisting of platinum (Pt), gold (Au), ruthenium (Ru), palladium (Pd), rhodium (Rh), iridium (Ir), osmium (Os), carbon (C), $WO_3$, $TiO_2$, and a conductive polymer.

In order to improve a redox catalyst efficiency, the side confronted by the first electrode may have a micro structure to increase the surface area. For example, it is desirable to form Pt or Au in a black state, and to form carbon in a porous structure. In the present embodiments, 'black state' means a state not supported by a supporter. Particularly, platinum black may be formed by performing anodic oxidation onto platinum or treating platinum with platinum chloride acid. The porous carbon may be formed by sintering a carbon particulate or baking an organic polymer.

The transparent substrate of the first electrode 11 may be joined with the transparent substrate of the first electrode 14 by using an adhesive, by using melt-fusion with an ultrasonic wave, heat, infrared rays, or vibration; or by welding. The electrolyte 13 is injected into the hole penetrating the second electrode 14 to be impregnated between the first electrode 11 and the second electrode 14. The electrolyte 13 is uniformly dispersed inside of the porous membrane in the light absorption layer 12.

The electrolyte 13 is formed of an electrolyte solution. The electrolyte solution is an iodide/triodide pair that receives and transfers electrons from the counter electrode to the dye through an oxidation-reduction reaction. The open circuit voltage is determined by a difference between the energy potential of the dye and the redox potential of the electrolyte.

The electrolyte solution may be a solution prepared by dissolving iodine in acetonitrile but it is not limited to the iodine acetonitrile solution and may be any substance that has hole conductivity.

The hole penetrating the second electrode 14 may be sealed with an adhesive or a cover glass. Although the present embodiment has been described with a liquid-phase electrolyte 13, a solid-phase electrolyte may also be used and this is also within the scope and range of the present embodiments.

The dye-sensitized solar cell having the above-described structure can be prepared by forming a first electrode with a conductive transparent substrate; forming a light absorption layer including a semiconductor particulate and a dye on one side of the first electrode; forming a second electrode; disposing the first electrode having the light absorption layer and the second electrode opposite to each other; and filling an electrolyte into a space between the first electrode and the second electrode and sealing the space.

In the present specification, the formation of the light absorption layer of the present embodiments, will be described.

First, a conductive transparent substrate is provided for a first electrode.

The first electrode may be made using a conventional method. For example, the first electrode may be fabricated by forming a conductive layer including a conductive material on a transparent substrate using electroplating, or a physical vapor deposition (PVD) method such as sputtering and electron beam deposition.

The rear side of a conductive transparent substrate is coated with a paste including a semiconductor particulate and heat treatment is performed to thereby form a porous semiconductor particulate layer on the transparent substrate.

The properties of the paste may be different according to how the substrate is coated. Generally, the substrate is coated with the paste in a doctor blade or screen printing method. To form a transparent layer, a spin-coating or spraying method is used. Alternatively, a general wet coating method can be used. The heat treatment is carried out at from about 400° C. to about 600° C. for about 30 minutes when a binder is added to the paste. In the case where no binder is added, the heat treatment may be performed at a temperature lower than about 200° C.

The porosity of the porous layer may be increased and maintained when a polymer is added to the porous semiconductor particulate layer and heat treatment is performed at from about 400° C. to about 600° C. Herein, a polymer that does not leave an organic material after the heat treatment should be selected. Examples of the polymer include ethylene cellulose (EC), hydroxy propyl cellulose (HPC), polyethylene glycol (PEG), polyethylene oxide (PEO), polyvinyl alcohol (PVA), and polyvinyl pyridone (PVP). Among the polymers, a polymer having an appropriate molecular weight in consideration of a coating method and coating conditions is selected. With an appropriate polymer added to the semiconductor particulate layer, a dispersion property as well as the porosity can be improved. Further, the layer can be better formed due to an increased viscosity and the adhesiveness to the substrate can be improved.

A dye layer can be formed by spraying a dye dispersion onto the semiconductor particulate layer or coating or impregnating the semiconductor particulate layer with or in the dye dispersion to adsorb the dye to the semiconductor particulate. The dye dispersion may further include at least one additive selected from the group consisting of compounds having the following formula 6 in order to improve photoelectric efficiency of a solar cell. The additive is the same as the above described. The additive may be used at a concentration of from about 0.3 to about 60 mM in the dye dispersion so that the additive may be from about 100 to about 3000 parts by weight based on 100 parts by weight of the dye in the light adsorption layer. According to one embodiment, the additive may be used at a concentration of from about 5 to about 40 mM The dye is naturally adsorbed to the semiconductor particulate when the first electrode having the semiconductor particulate layer is immersed by a dye dispersion for about 12 hours. The dye is the same as described above, and the solvent dispersing the dye is not limited to a specific solvent. Examples of the solvent include acetonitrile, dichloromethane, and an alcohol-based solvent.

The dye dispersion where the dye is dispersed may further include an organic pigment of a variety of colors to improve the long-wavelength visible ray absorption and to improve the dye adsorption efficiency. Examples of the organic pigment include cumarine, pheophorbide A, and a porphyrin.

After the dye layer is formed, a light absorption layer can be prepared by washing out the dye that is not adsorbed, through solvent washing.

The second electrode is prepared by forming a conductive layer including a conductive substance on a conductive transparent substrate using electroplating, or a physical vapor deposition (PVD) method, such as, sputtering, and electron beam deposition.

The first electrode and the second electrode are disposed such that the light absorption layer contacts the second electrode. Then, the space between the light absorption layer and the second electrode is filled with the electrolyte and sealed to thereby prepare the dye-sensitized solar cell of the present embodiment.

The first electrode and the second electrode contact each other face to face by using an adhesive agent. The adhesive agent may be a thermoplastic polymer film, such as Surlyn produced by the duPont Company (Wilmington, Del.). The thermoplastic polymer film is placed between the two electrodes and heat and pressure are applied to the electrodes. An epoxy resin or an ultraviolet (UV) ray initiator may be used as the adhesive agent. The adhesion may be hardened after heat treatment or UV treatment.

The following examples illustrate the present embodiments in more detail. However, it is understood that the present embodiments are not limited by these examples.

Example 1

Fabrication of a Dye-Sensitized Solar Cell

A dye (5) was synthesized in accordance with the following Reaction Scheme 1. Referring to Reaction Scheme 1, the synthesis of the dye (5) will be described in more detail. iodine, periodic acid, distilled water, sulfuric acid, and acetic acid were added to fluorene (Aldrich Company, St. Louis, Mo.) and then reaction was performed at 90° C. until an iodine color in the resulting the mixed solution disappeared. After the reaction was complete, an excessive amount of distilled water was added to the mixed solution which was then filtered using a Buchner funnel. The filtrate was rinsed with water and dried. A small amount of acetone was added to the dried product and maintained at a low temperature to obtain pale yellow 2-iodo-9-fluorene (5a).

Then, tetrahydrofuran was added to the prepared 2-iodo-9-fluorene (5a), and thereafter potassium tertiary butoxide was slowly added to the resulting mixture at 0° C. and iodomethane (Aldrich Co.) was additionally added, preparing a mixed solution. The mixed solution was agitated for about one hour and then distilled to remove a solvent therein. The acquired dry product was separated by using chromatography, obtaining a pure white product of 2-iodo-9,9-dimethyl-fluorene (5b). Herein, an eluent was prepared by mixing dichloromethane and hexane in a volume ratio of 1:10.

Then, copper iodide and potassium hydroxide were added to the prepared 2-iodo-9,9-dimethyl-fluorene (5b). The resulting mixture was reacted in toluene at a temperature of higher than 130° C. for 20 hours. When the reaction was complete, the mixed solution was distilled to remove solvent. The acquired dry product was extracted with dichloromethane and then separated by using chromatography, obtaining N,N-bis(9,9-dimethylfluorene-2-nyl)aniline (5c). Herein, an eluent was prepared by mixing dichloromethane and hexane in a volume ratio of 1:10.

Then, tetrakis (triphenylphosphine) as a catalyst was added to the prepared N,N-bis(9,9-dimethylfluorene-2-nyl)-4-bromoaniline (5c), and a 2-thiophene boric acid (Aldrich Co.) aqueous solution was additionally added thereto. The resulting mixed solution was maintained at 90° C. for 15 hours. The mixed solution was cooled to room temperature, and its solvent was all removed. The resulting product was separated by using chromatography, obtaining a yellow solid, 2-[N,N-bis(9,9-dimethylfluorene-2-nyl)phenyl]thiophene (5d). Herein, an eluent was prepared by mixing ethylene acetate and hexane in a volume ratio of 1:10.

Next, dimethylformamide was added to the prepared 2-[N,N-bis(9,9-dimethylfluorene-2-nyl)phenyl]thiophene (5d), and phosphorus oxychloride was slowly added thereto at 0° C. The mixed solution was reacted at room temperature for 30 minutes. When the reaction was complete, the mixed solution was distilled to all remove all solvent. Then, a dry product was separated by using chromatography, obtaining a red solid, 5-[N,N-bis(9,9-dimethylfluorene-2-nyl)phenyl]-thiophene-2-carboxylaldehyde (5e). Herein, an eluent was prepared by mixing ethylacetate and hexane in a volume ratio of 1:1.

Then, cyanoacetic acid and acetonitrile were added to the prepared 5-[N,N-bis(9,9-dimethylfluorene-2-nyl)phenyl]-thiophene-2-carboxylaldehyde (5e), and piperidine was also added thereto. The resulting mixed solution was heated for 12 hours. When the reaction was complete, the mixed solution was distilled to remove solvent. The resulting dry product was dissolve in dichloromethane and thereafter washed with water to extract dichloromethane organic solvent and dried with magnesium sulfate ($MgSO_4$) as a desiccant. The resulting dry product was separated by using chromatography, obtaining 3-{5-[N,N-bis(9,9-dimethylfluorene-2-nyl)phenyl]-thiophene-2-nyl}-2-cyanoacrylic acid (5). Herein, an eluent was prepared by mixing ethylacetate and hexane in a volume ratio of 1:1.

A titanium oxide dispersion solution including titanium oxide particles with a particle diameter of 5 to 15 nm was applied to 1 $cm^2$ of an indium-doped tin oxide transparent conductor by using a doctor blade method, and heat treatment was performed at 450° C. for 30 minutes to thereby form a 18 μm-thick porous titanium oxide layer. The 18 μm-thick porous titanium oxide layer was maintained at 80° C. and immersed in a 0.3 mM dye dispersion solution, which was prepared by dissolving the compound having a structure of the prepared Formula 5 in ethanol, to adsorb a dye for over 12 hours. The dye-adsorbed porous titanium oxide layer was washed with ethanol and dried at room temperature to thereby form a first electrode with a light absorption layer formed thereon.

A second electrode was prepared by depositing a 200 nm-thick Pt layer on an indium-doped tin oxide transparent conductor by sputtering and forming a fine hole with a drill having a diameter of 0.75 mm to inject an electrolyte solution.

A 60 μm-thick thermoplastic polymer film was disposed between the first electrode and the second electrode and pressure was applied to the first and second electrodes at 100° C. for 9 seconds to adhere the two electrodes. An oxidation-reduction electrolyte was injected through the fine hole formed in the second electrode, and the fine hole was sealed up by using a cover glass and a thermoplastic polymer film to thereby fabricate a dye-sensitized solar cell. The oxidation-reduction electrolyte was prepared by dissolving 0.62M 1,2-dimethyl-3-hexylimidazolium iodide, 0.5M 2-aminopyrimidine, 0.1M LiI, and 0.05M $I_2$ in an acetonitrile solvent.

[Reaction Scheme 1]

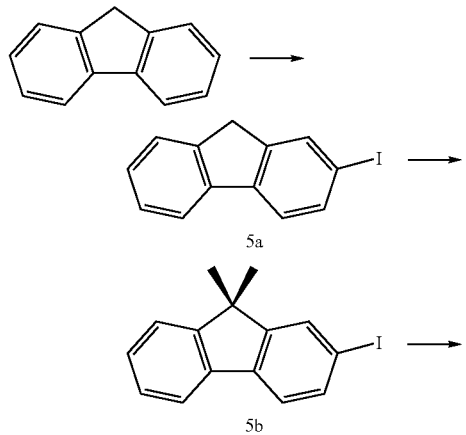

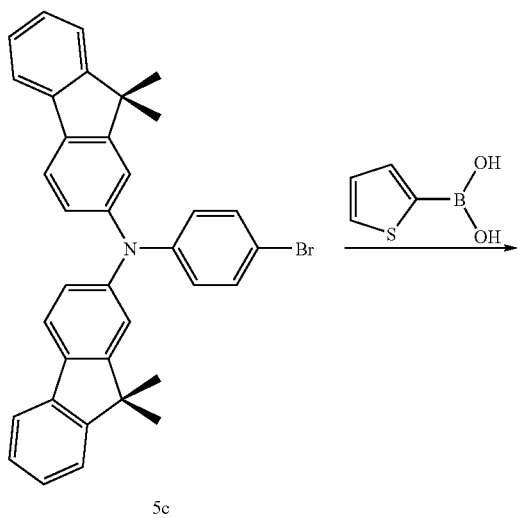

5c

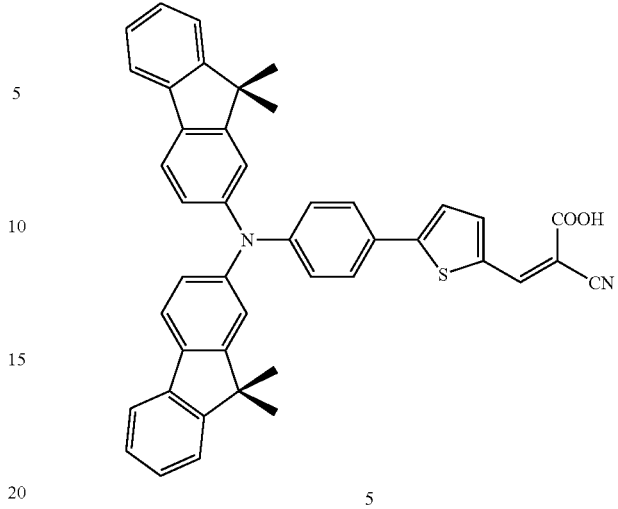

5

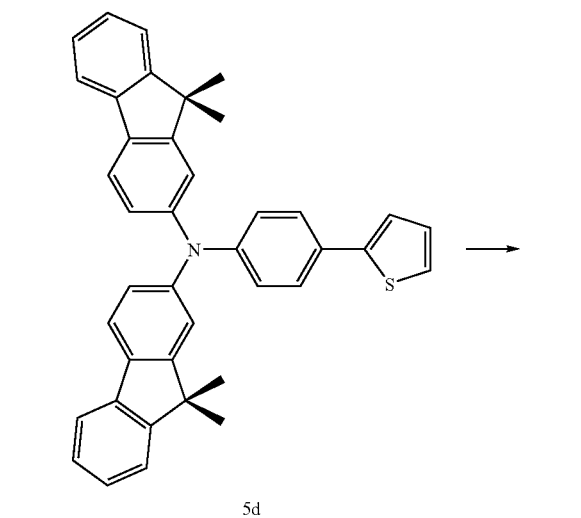

5d

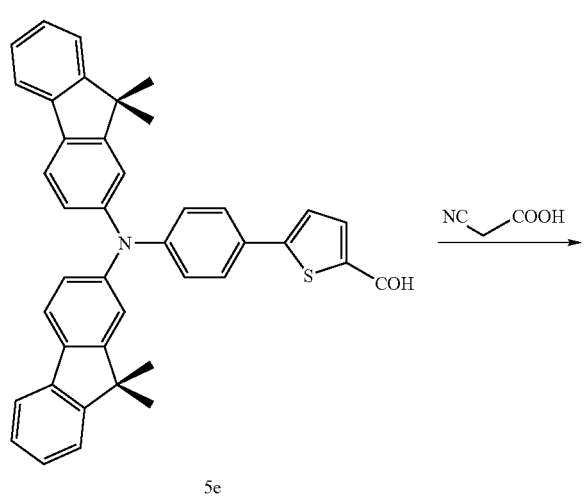

5e

Example 2

Fabrication of a Dye-Sensitized Solar Cell

As shown in the following Reaction Scheme 2, a tetrakis(triphenyl phosphine) catalyst was added to the N,N-bis(9,9-dimethylfluorene-2-nyl)-4-bromoaniline (5c) according to Example 1, and tetrahydrofuran was added to 2,2'-bithiophene (Aldrich Co.). Then, normal butyllithium was added to the resulting mixture at −78° C., preparing a mixed solution. The mixed solution was maintained at room temperature, and trimethylborate (Aldrich Co.) was added thereto. Hydrated 5-{2,2'-bithiophene}boric acid) (5f) aqueous solution was added thereto. The resulting mixed solution was maintained at 90° C. for 15 hours. The mixed solution was cooled to room temperature, and after its solvent was all removed, it was separated by using chromatography, obtaining a light yellow solid, 2-[N,N-bis(9,9-dimethylfluorene-2-nyl)phenyl]-5,5'-bithiophene 5g. Herein, an eluent was prepared by mixing ethylene acetate and hexane in a volume ratio of 1:10.

Then, dimethylformamide was added to the prepared 2-[N,N-bis(9,9-dimethylfluorene-2-nyl)phenyl]-5,5'-bithiophene (5g), and phosphorus oxychloride was slowly added thereto at 0° C. The prepared mixed solution was maintained at room temperature for 30 minutes. When the reaction was complete, the mixed solution was distilled to remove its solvent. The acquired dry product was separated by using chromatography, obtaining a red solid, 5'-[N,N-bis(9,9-dimethylfluorene-2-nyl)phenyl]-2,2'-bithiophene-5-carboxylaldehyde (5h). Herein, an eluent was prepared by mixing ethyl acetate and hexane in a volume ratio of 1:1.

Then, acetonitrile was added to the prepared 5'-[N,N-bis(9,9-dimethylfluorene-2-nyl)phenyl]-2,2'-bithiophene-5-carboxylaldehyde (5h) and cyanoacetic acid, and piperidine was added thereto. The resulting mixed solution was heated for 12 hours to remove a solvent therein. The acquired dry product was dissolved in dichloromethane and then washed with water. Next, a dichloromethane organic solvent was extracted. Herein, magnesium sulfate ($MgSO_4$) was used for drying. The resulting dry product was separated by using chromatography, yielding 3-{5'-[N,N-bis(9,9-dimethylfluorene-2-nyl)phenyl]-2,2'-bithiophene-5-nyl}-2-cyano-acrylic acid (6). Herein, an eluent was prepared by mixing ethylacetate and hexane in a volume ratio of 1:1.

A dye-sensitized solar cell was fabricated according to the same method as in Example 1, except that the compound of the prepared Formula 6 for a dye was used.

[Reaction Scheme 2]

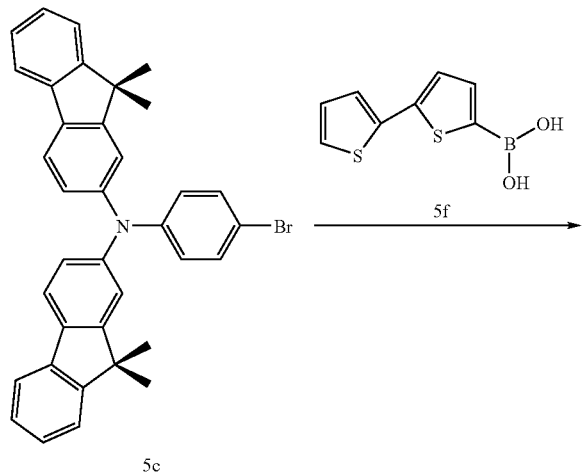

5c

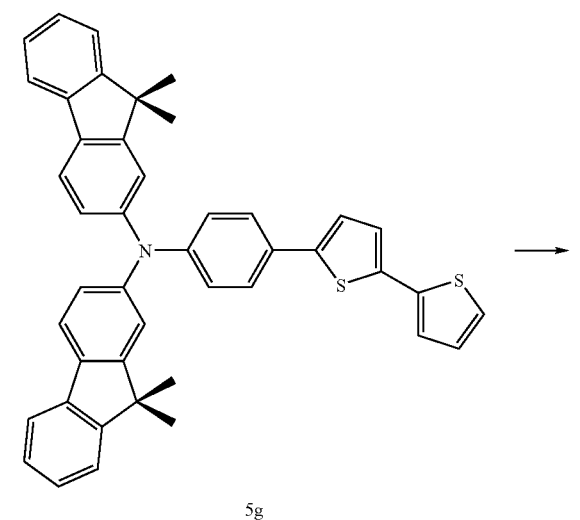

5g

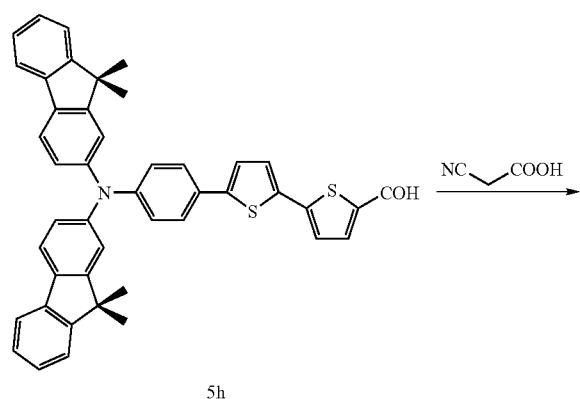

5h

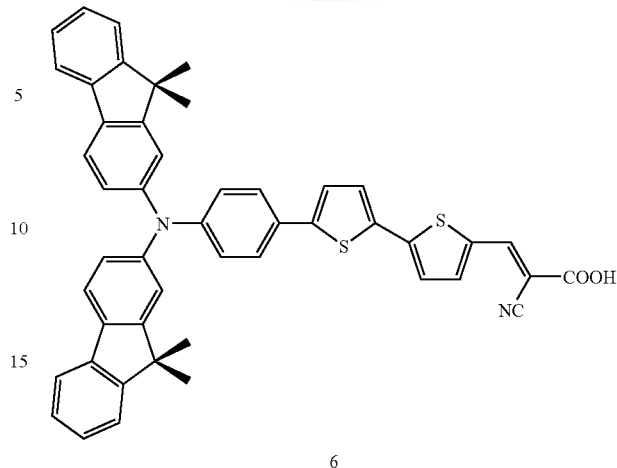

6

Example 3

Fabrication of Dye-Sensitized Solar Cell

A dye-sensitized solar cell was fabricated according to the same method as in Example 1, except that 5 mM deoxycholic acid of the following Formula 12 was further added to the dye dispersion.

[Chemical Formula 12]

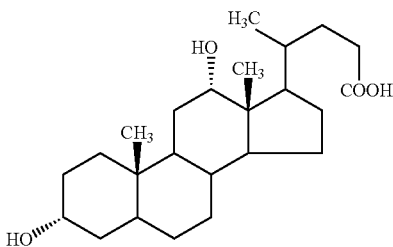

Example 4

Fabrication of Dye-Sensitized Solar Cell

A dye-sensitized solar cell was fabricated according to the same method as in Example 1, except that 40 mM deoxycholic acid of the above Formula 12 was further added to the dye dispersion.

Example 5

Fabrication of Dye-Sensitized Solar Cell

A dye (9) was synthesized according to the following Reaction Scheme 3. Illustrating the synthesis process of the dye (9) with reference to Reaction Scheme 3, 1.00 g (3.8 mmol) of 2-iodo-5-nitrophenol acetate 9a, 2-trimethylsilylacetyl-5-thiophene-carboxylaldehyde, 1.11 g (3.8 mmol) of 2,2-dimethylpropane-1,3-dyl acetal (9b), 1.05 g (7.6 mmol) of $K_2CO_3$, 5 mol % of $Pd(PPh_3)_4$, and 5 mol % of CuI were dissolved in a mixed solvent of 10 mL of dimethylamine and 50 mL of acetonitrile, preparing a mixed solution. The mixed solution was refluxed and agitated for 8 hours and thereafter cooled to room temperature. Then, 30 mL of water and 50 mL of dichloromethane were added to the above mixed solution, extracting an organic layer. The organic layer was primarily dried with MgSO₄ and secondarily dried under vacuum. Then, chromatography was performed on it by using silica gel, separating a compound (9c).

Next, 30 mL of methanol, 0.020 g of Raney nickel, and 0.097 mL (2 mmol) of hydrazine hydrate were mixed to prepare a solution. The mixed solution was heated to a temperature of 55 to 60° C. Thereafter, the separated compound (9c) was added to the resulting mixed solution, which was then, refluxed and agitated for 5 hours. The Raney nickel in the resulting mixed solution was filtered and then dried. The dry product was added to a mixed solution of 30 mL of water and 50 mL of dichloromethane, extracting an organic layer. The organic layer was dried with MgSO₄ and then dried under vacuum. Then, chromatography was performed by using silica gel, separating a compound (9d) including a nitro substituent.

0.2 g (0.6 mmol) of the compound (9d) was dissolved with 0.42 g (1.3 mmol) of 2-iodo-9,9-dimethylfluorene, 0.36 g (2.7 mmol) of potassium carbonate, 0.13 g (0.2 mmol) of copper, and 0.02 g (0.07 mmol) of 18-crown-6 in 40 mL of 1,2-dichlorobenzene and then refluxed and agitated for 48 hours, preparing a mixed solution. The mixed solution was cooled down, and an inorganic particulate therein was filtered and removed. Then, an ammonia solution and water were mixed with the remaining solution and agitated, extracting an organic layer. The organic layer was primarily dried with MgSO₄ and secondarily dried under vacuum. Chromatography was then performed on the dry product, separating a compound (9e).

Next, 0.1 g (0.14 mmol) of the separated compound (9e) was added to a mixed solvent of 30 mL of tetrahydrofuran and 10 mL of water, and 2 mL of trifluoroacetic acid was slowly added in a dropwise fashion, preparing a mixed solution. The mixed solution was agitated at room temperature for 2 hours, and sodium bicarbonate and water were added thereto for neutralization. Then, 50 mL of dichloromethane was added to the mixed solution, extracting an organic layer. The organic layer was dried with MgSO₄ and then dried under vacuum. Then, chromatography was performed on it by using silica gel, separating a compound (9f).

0.03 g (0.05 mmol) of the compound (9f) was added to 0.01 g (0.1 mmol) of cyanoacetic acid. Then, they were mixed with a mixed solvent of 60 mL of acetonitrile and 0.003 mL of piperidine, preparing a mixed solution. This mixed solution was refluxed and agitated for 6 hours and then cooled to room temperature, extracting an organic layer. The organic layer was vacuum-dried, and chromatography was performed by using a silica gel, separating compound (9).

[Reaction Scheme 3]

9a

-continued

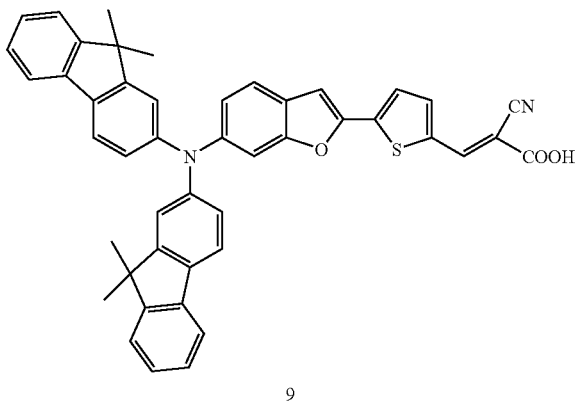 [SMILES: CC1(C)c2ccccc2-c2ccc(N(c3ccc4c(c3)C(C)(C)c3ccccc3-4)c3ccc4cc(-c5ccc(/C=C(\C#N)C(=O)O)s5)oc4c3)cc21]

9

An oxidation titanium dispersion solution having a particle diameter ranging from 5 to 15 nm was coated to be 1 cm² on a transparent tin oxide conductor doped with indium in a doctor blade method. The resulting product was fired at 450° C. for 30 minutes, preparing a porous oxidation titanium membrane. The porous oxidation titanium membrane was maintained at 80° C. and then dipped in a mixed solution of 0.3 mM dye dispersion solution, in which a compound with the above Formula 9 was dissolved in ethanol, and deoxycholic acid was added thereto at a concentration of 10 mM to perform a dye adsorption treatment for 12 hours.

Next, the porous oxidation titanium membrane absorbed with a dye was washed with ethanol and dried at room temperature, preparing a first electrode with a light absorption layer.

As for a second electrode, a Pt layer was disposed to be about 200 nm thick on a transparent oxidized tin conductor doped with indium by sputtering. Then, a minute hole was formed by using a drill with a 0.75 mm diameter to inject an electrolyte solution, preparing a second electrode.

The first and second electrodes were compressed at 100° C. for 9 seconds after a 60 μm-thick thermoplastic polymer film was interposed therebetween. Then, an oxidation-reduction electrolyte was injected through the hole in the second electrode. The hole was sealed by using a cover-glass and a thermoplastic polymer film, fabricating a dye-sensitized solar cell. Herein, the oxidation-reduction electrolyte was prepared by dissolving 0.62M of 1,2-dimethyl-3-hexylimidazolium iodide, 0.5M of 2-aminopyrimidine, 0.1 M of LiI, and 0.05M of 12 in an acetonitrile solvent.

Example 6

Fabrication of a Dye-Sensitized Solar Cell

A dye (10) was synthesized according to the following Reaction Scheme 4. Illustrating the synthesis process of the dye (10) in more detail with reference to Reaction Scheme 4, 6.5 g (20.3 mmol) of 2-iodo-9,9-dimethylfluorene (10a), 1.37 g (9.23 mmol) of 6-aminobenzo[b]thiophene (10b), 5.62 g (40.6 mmol) of potassium carbonate, 1.93 g (30.5 mmol) of copper, and 0.29 g (1.11 mmol) of 18-crown-6 were dissolved in 70 mL of 1,2-dichlorobenzene, preparing a mixed solution that was refluxed and agitated for 48 hours. The mixed solution was cooled down, and an undissolved inorganic material therein was filtrated and removed. Then, an ammonia aqueous solution and water were mixed with the remaining solution, and the resulting solution was agitated to extract an organic layer. The organic layer was primarily dried with MgSO₄ and secondarily dried under vacuum, and then chromatography was performed by using a silica gel, separating a compound (10c).

0.5 g (0.93 mmol) of the separated compound (10c) was dissolved in 50 mL of Et₂O, and 0.64 mL (1.6 M hexane) of n-butyllithium was slowly added thereto in a dropwise fashion, preparing a mixed solution. 3 hours later, 0.16 g (1.03 mmol) of bromine was slowly added to the mixed solution at 0° C. in a dropwise fashion, preparing a mixed solution. The mixed solution was mixed with a 5% KOH aqueous solution for neutralization, extracting an organic layer. The organic layer was primarily dried with MgSO₄ and secondarily dried under vacuum, and thereafter chromatography was performed on it by using a silica gel, separating a compound (10d).

0.4 g (0.65 mmol) of the compound 10d, 0.47 g (0.97 mmol) of tributyl(5-(5,5-dimethyl-1,3-dioxane-2-yl)thiophene-2-yl)stannane, and 0.075 g (0.065 mmol) of Pd(PPh₃)₄ were dissolved in 50 mL of toluene, preparing a mixed solution. The mixed solution was refluxed and agitated for 12 hours and cooled to room temperature. Then, 30 mL of water and 50 mL of dichloromethane were added to the mixed solution, extracting an organic layer. The organic layer was dried with MgSO₄ and then dried under vacuum, and then chromatography was performed on it by using a silica gel, separating a compound 10e.

Next, 30 mL of tetrahydrofuran and 10 mL of water were added to a flask containing 0.3 g (0.41 mmol) of the compound (10e), preparing a mixed solution, and 3 mL of trifluoroacetic acid was slowly add thereto in a dropwise fashion. The resulting mixed solution was agitated at room temperature for 2 hours, and thereafter sodium bicarbonate and water were added thereto for neutralization. The mixed solution was agitated, and thereafter an organic layer was extracted therefrom by using 50 mL of dichloromethane. The organic layer was primarily dried with MgSO₄ and secondarily dried under vacuum, and then chromatography was performed on it by using a silica gel, separating a compound (10f).

Next, 0.26 g (0.40 mmol) of the compound (10f) and 0.07 g (0.80 mmol) of cyanoacetic acid were dried under vacuum, and then 60 mL of acetonitrile and 0.039 mL (0.40 mmol) of piperidine were added thereto, preparing a mixed solution. The mixed solution was refluxed and agitated for 6 hours and cooled to room temperature, extracting an organic layer. The organic layer was vacuum-dried, and then chromatography was performed on silica gel, separating compound (10).

[Reaction Scheme 4]
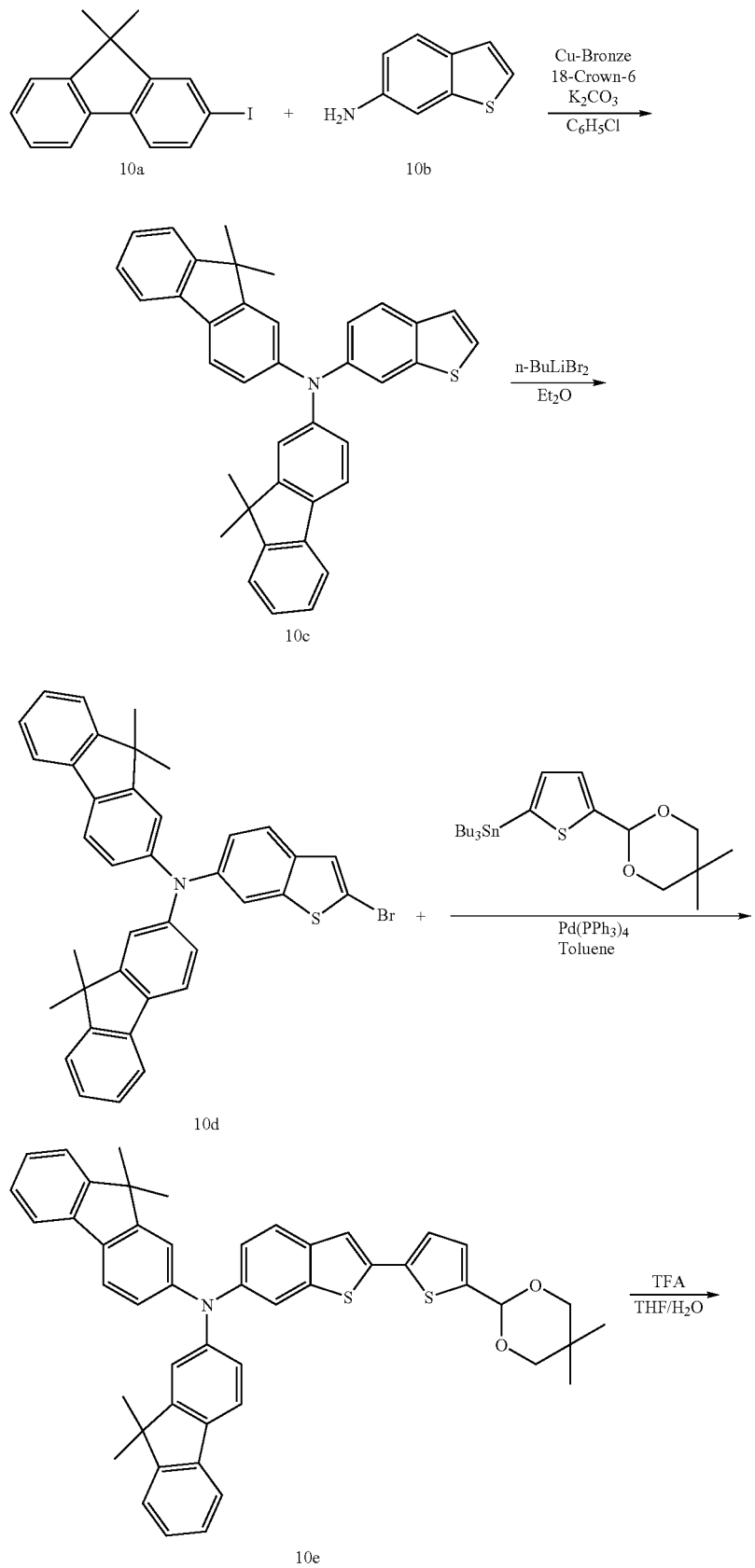

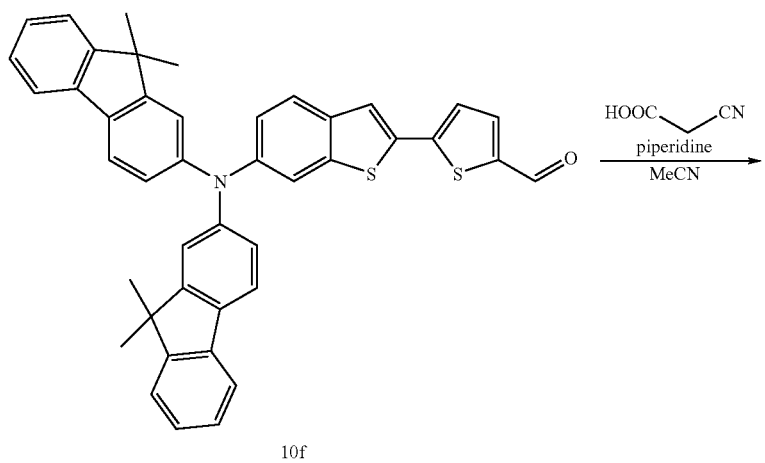

10f

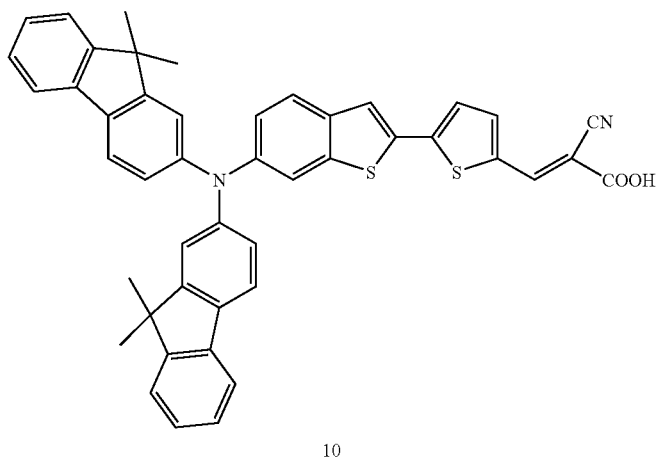

10

A dye-sensitized solar cell was fabricated according to the same method as in Example 1, except for using a compound with a structure represented by the above Formula 10 as a dye.

Example 7

Fabrication of a Dye-Sensitized Solar Cell

A dye-sensitized solar cell was fabricated according to the same method as in Example 5, except that deoxycholic acid of the above Formula 12 was increased up to a concentrations of 5 mM in a dye dispersion solution.

Example 8

Fabrication of a Dye-Sensitized Solar Cell

As shown in the following Reaction Scheme 5, rhodanine acetic acid, ammonium acetate, and acetic acid as a solvent were added to 5-[N,N-bis(9,9-dimethylfluorene-2-nyl)phenyl]-thiophene-2-carboxylaldehyde (5e) of Example 1, preparing a mixed solution. The mixed solution was heated at 120° C. for one hour and cooled to room temperature. Then, a solvent in the mixed solution was all removed, obtaining a dry product. The dry product was dissolved in dichloromethane and washed with water, extracting a dichloromethane organic solvent. It was dried with magnesium sulfate ($MgSO_4$). The acquired dry product was separated by using chromatography, preparing 2-(5-((5-(4-(bis(9,9-dimethyl-fluorene-2-nyl)amino)phenyl)thiophene-2-nyl)methylene)-4-oxo-thioxo-thiazolidine-3-nyl)acetic acid 7. Herein, an eluent was prepared by mixing ethylacetate and hexane in a volume ratio of 1:1 (methanol).

Then, a dye-sensitized solar cell was fabricated according to the same method as in Example 3, except for using a compound with a structure represented by the above Formula 7 as a dye.

[Reaction Scheme 5]

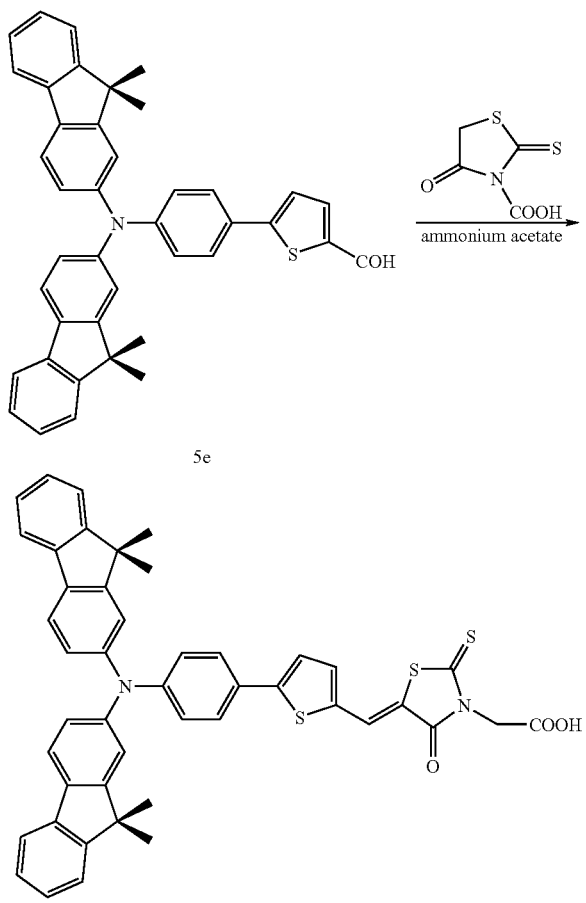

Example 9

Fabrication of a Dye-Sensitized Solar Cell

As shown in the following Reaction Scheme 6, rhodanine acetic acid, ammonium acetate, and acetic acid as a solvent were added to 5'-[N,N-bis(9,9-dimethylfluorene-2-nyl)phenyl]-2,2'-bithiophene-5-carboxylaldehyde 5h prepared according to Example 2, preparing a mixed solution. The mixed solution was heated at 120° C. for one hour and cooled to room temperature. Then, the solvent in the mixed solution evaporated, yielding a dry product. The dry product was dissolved in dichloromethane and thereafter washed with water, extracting a dichloromethane organic solvent. The dichloromethane organic solvent was dried with magnesium sulfate ($MgSO_4$). The acquired dry product was separated by using chromatography, acquiring 2-(5-((5-(4-(bis(9,9-dimethyl-fluorene-2-nyl)amino)phenyl)2,2'-bithiophene-5-nyl)methylene)-4-oxo-2-thioxo-thiazolidine-3-nyl)acetic acid (8). Herein, an eluent was prepared by mixing ethylacetate and hexane in a volume ratio of 1:1 (methanol).

Then, a dye-sensitized solar cell was fabricated according to the same method as in Example 3, except for using a compound with a structure represented by the above Formula 8 as a dye.

[Reaction Scheme 6]

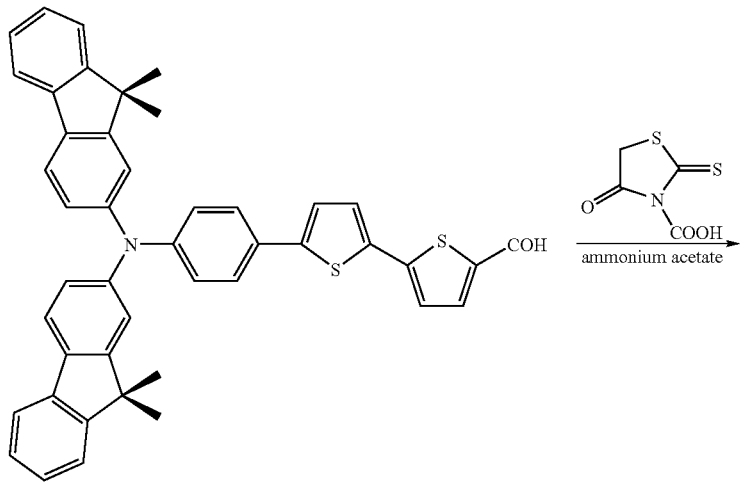

5h

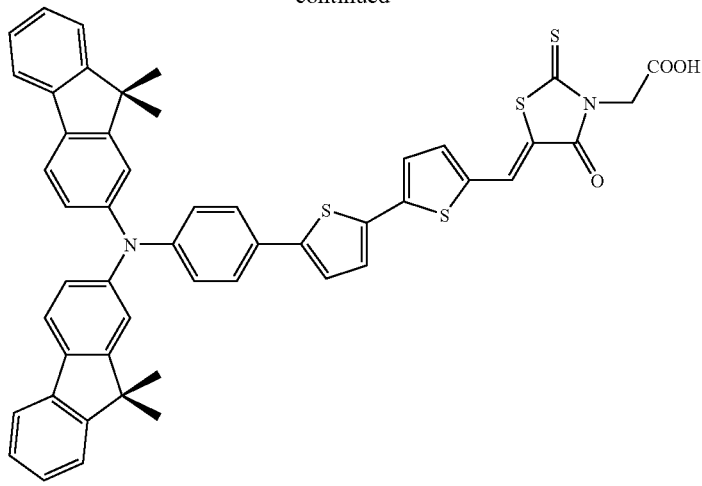

8

Comparative Example 1

Fabrication of a Dye-Sensitized Solar Cell

A titanium oxide dispersion solution including titanium oxide particles with a particle diameter of 5 to 15 nm was applied to 1 cm² of an indium-doped tin oxide transparent conductor by using a doctor blade method, and a heat treatment was performed at 450° C. for 30 minutes to thereby form a 18 μm-thick porous titanium oxide layer. The 18 μm-thick porous titanium oxide layer was maintained at 80° C. and immersed in a 0.3 mM dye dispersion solution, which was prepared by dissolving the compound having a structure of Formula 13 in ethanol, to adsorb a dye for over 12 hours. The dye-adsorbed porous titanium oxide layer was washed with ethanol and dried at room temperature to thereby form a first electrode with a light absorption layer formed thereon.

A second electrode was prepared by depositing a 200 nm-thick Pt layer on an indium-doped tin oxide transparent conductor by sputtering and forming a fine hole with a drill having a diameter of 0.75 mm to inject an electrolyte solution therein.

A 60 μm-thick thermoplastic polymer film was disposed between the first electrode and the second electrode and pressure was applied to the first and second electrodes at 100° C. for 9 seconds to adhere the two electrodes. An oxidation-reduction electrolyte was injected through the fine hole formed in the second electrode, and the fine hole was sealed up by using a cover glass and a thermoplastic polymer film to thereby fabricate a dye-sensitized solar cell. The oxidation-reduction electrolyte was prepared by dissolving 0.62 M 1,2-dimethyl-3-hexylimidazolium iodide, 0.5M 2-aminopyrimidine, 0.1 M LiI, and 0.05M I2 in an acetonitrile solvent.

[Chemical Formula 13]

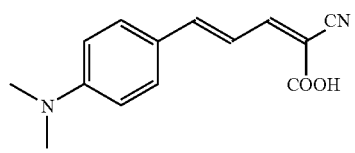

Comparative Example 2

Fabrication of a Dye-Sensitized Solar Cell

A dye-sensitized solar cell was fabricated according to the same method as in Comparative Example 1, except that the compound of the following Formula 14 for a dye was used.

[Chemical Formula 14]

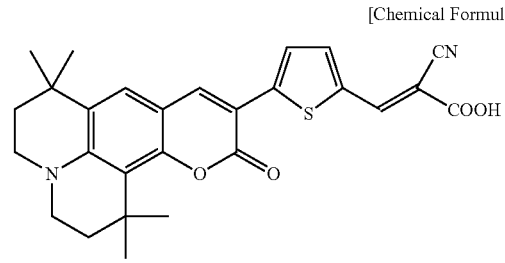

Comparative Example 3

Fabrication of a Dye-Sensitized Solar Cell

A dye-sensitized solar cell was fabricated according to the same method as in Comparative Example 1, except that the compound of the following Formula 15 for a dye was used.

[Chemical Formula 15]

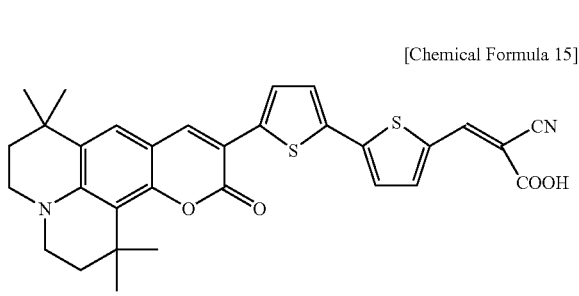 [SMILES: CC1(C)CCN2CCC(C)(C)c3c2c1cc1cc(-c2ccc(-c4ccc(/C=C(/C#N)C(=O)O)s4)s2)c(=O)oc31]

Comparative Example 4

Fabrication of a Dye-Sensitized Solar Cell

A dye-sensitized solar cell was fabricated according to the same method as in Comparative Example 3, except that 40 mM deoxycholic acid of the above Formula 7 was further added to the dye dispersion.

Comparative Example 5

Fabrication of a Dye-Sensitized Solar Cell

A dye-sensitized solar cell was fabricated according to the same method as in Comparative Example 1, except that 10 mM deoxycholic acid of the above Formula 7 was further added to the dye dispersion.

Comparative Example 6

Fabrication of a Dye-Sensitized Solar Cell

A dye-sensitized solar cell was fabricated according to the same method as in Comparative Example 2, except that 10 mM deoxycholic acid of the above Formula 7 was further added to the dye dispersion.

Comparative Example 7

Fabrication of a Dye-Sensitized Solar Cell

A dye-sensitized solar cell was fabricated according to the same method as in Comparative Example 3, except that 10 mM deoxycholic acid of the above Formula 7 was further added to the dye dispersion.

Photocurrent voltages of the dye-sensitized solar cells according to the Examples 1 to 6 and Comparative Examples 1 to 7 were measured, and the open-circuit voltage (Voc), current density (short-circuit current: Jsc), and a fill factor (FF) were calculated based on a curve line of the measured photocurrent voltages. From the results, solar cell efficiency was evaluated.

Herein, a xenon lamp of Oriel (Newport Corporation, Irvine, Calif.), 01193, was used as a light source, and the solar condition (AM 1.5) of the xenon lamp was corrected by using a standard solar cell (Frunhofer Institute Solare Engeriessysteme, Certificate No. C-ISE369, Type of material: Mono-Si+ KG filter). The measurement results are shown in the following Table 1 and FIGS. 2 and 3.

TABLE 1

| | Open-circuit voltage (V) | Current density (mA/cm$^2$) | F.F | Efficiency (%) |
|---|---|---|---|---|
| Example 1 | 0.69 | 10.71 | 64 | 4.72 |
| Example 2 | 0.66 | 10.71 | 66 | 4.67 |
| Example 3 | 0.67 | 11.61 | 66 | 5.15 |
| Example 4 | 0.69 | 12.16 | 71 | 5.96 |
| Example 5 | 0.70 | 14.39 | 66 | 6.65 |
| Example 6 | 0.74 | 15.33 | 66 | 7.43 |
| Comparative Example 1 | 0.53 | 4.57 | 53 | 1.29 |
| Comparative Example 2 | 0.55 | 7.35 | 64 | 2.61 |
| Comparative Example 3 | 0.56 | 9.07 | 58 | 2.91 |
| Comparative Example 4 | 0.57 | 10.61 | 65 | 3.93 |
| Comparative Example 5 | 0.53 | 4.57 | 53 | 1.29 |
| Comparative Example 6 | 0.55 | 7.35 | 64 | 2.61 |
| Comparative Example 7 | 0.56 | 9.07 | 58 | 2.91 |

As shown in Table 1, the open circuit voltage (Voc) of the solar cells according to Examples 1 to 6 was greater than 0.66V, and the open circuit voltage of the solar cell of Comparative Examples 1 to 7 was less than 0.60V. The current densities and fill factors of dye-sensitized solar cells according to Examples 1 to 6 are higher than those of Comparative Examples 1 to 7, indicating that the dye-sensitized solar cells according to Examples 1 to 6 showed remarkably better photoelectric efficiency than those of Comparative Examples 1 to 7. From these results, it is indicated that the dyes included in the dye-sensitized solar cell according to Examples 1 to 6 show better efficiency over the dye used in the solar cells according to Comparative Examples 1 to 7.

As a comparison result of the solar cells according to Examples 1 and 2 and the solar cells according to Examples 3 and 4, the solar cells according to Examples 3 and 4 including the deoxycholic acid additive showed more improved characteristics in terms of open-circuit voltage, current density, fill factor, and photoelectric efficiency over those of Examples 1 and 2. Such photoelectric efficiency improvement increases as the additive concentration increases.

Figure 2:
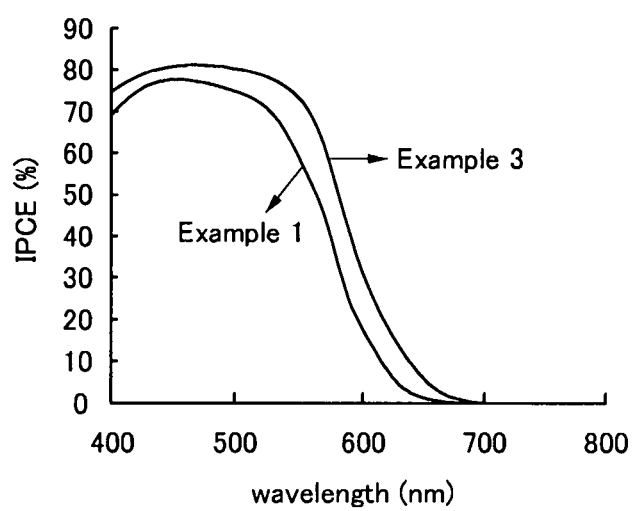
FIG. 2 shows incident photon-to-current efficiency (IPCE) of the solar cells according to Examples 1 and 3.

FIG. 2 shows incident photon-to-current efficiency (IPCE) of the solar cells according to Examples 1 and 3.

As shown in FIG. 2, the solar cell including both the fluorenyl-containing organic dye and the additive according to Example 3 shows a higher photon-to-current efficiency than that of Example 1 including only the fluorenyl-containing organic dye at a predetermined wavelength. The organic dye including the fluorenyl functional group is adsorbed along with the deoxycholic acid on TiO$_2$ and thereby increases current over when using only the organic dye including the fluorenyl functional group.

Figure 3:
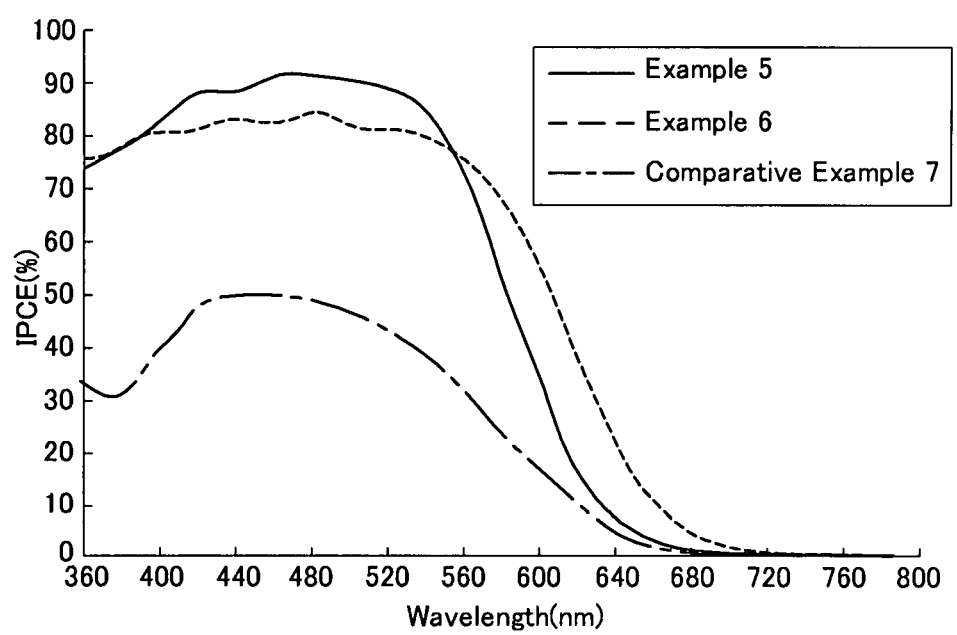
FIG. 3 shows incident photon-to-current efficiency (IPCE) of the solar cells according to the Examples 5 and 6, and Comparative Example 7.

In addition, FIG. 3 is a graph showing incident photon to current efficiency (IPCE) of the dye-sensitized solar cells of Examples 5 and 6 and Comparative Example 7 by wavelength.

In general, when a dye has a photocharge yield of 80%, it can be said to have excellent incident photon to current efficiency (IPCE). As shown in FIG. 3, that of Example 5 had a photocharge yield of 90%, and that of Example 6 had about 83%. However, that of Comparative Example 7 had a photocharge yield of only 50%.

Therefore, when a dye for a dye-sensitized solar cell of the present embodiments is applied to a light absorption layer of a dye-sensitized solar cell, it can improve incident photon to current efficiency (IPCE) and thereby, open-circuit voltage.

While the present embodiments have been described in connection with what is presently considered to be practical exemplary embodiments, it is to be understood that the present embodiments are not limited to the disclosed embodiments, but, on the contrary, is intended to cover various modifications and equivalent arrangements included within the spirit and scope of the appended claims.

What is claimed is:

1. A dye for a dye-sensitized solar cell wherein the dye is selected from the group consisting of the compounds of the following Chemical Formulae 7 and 8:

[Chemical Formula 7]

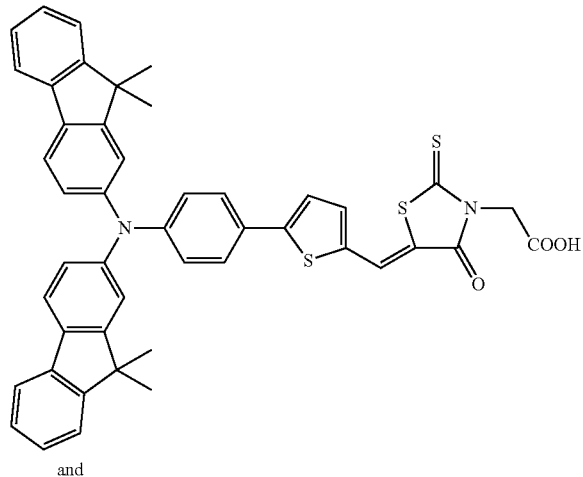

and

[Chemical Formula 8]

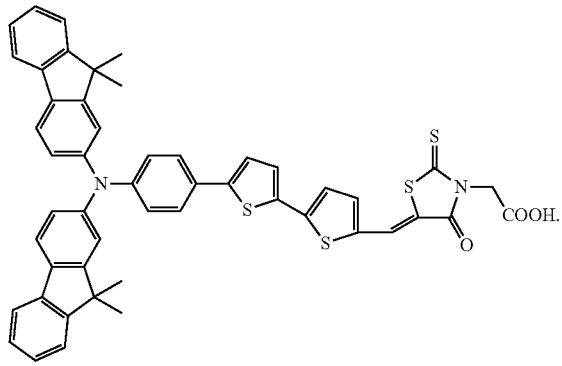

2. A dye for a dye-sensitized solar cell wherein the dye is a compound of the following Chemical Formula 7:

[Chemical Formula 7]

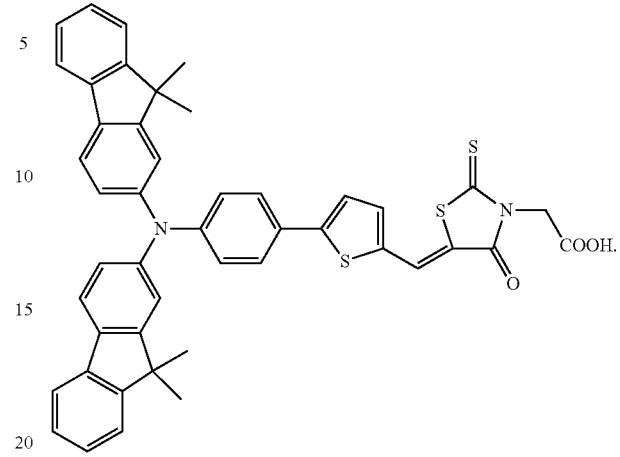

3. A dye for a dye-sensitized solar cell wherein the dye is a compound of the following Chemical Formula 8:

[Chemical Formula 8]

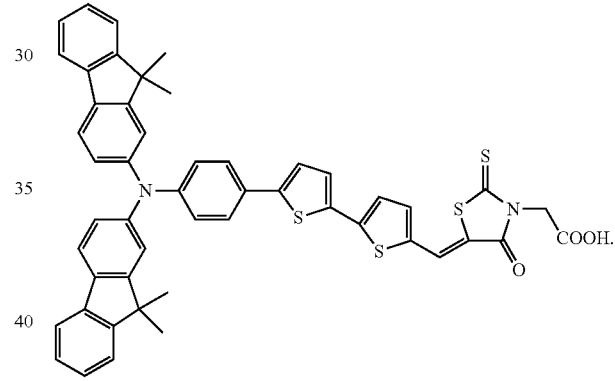

* * * * *